(12) United States Patent  
Smith et al.

(10) Patent No.: US 12,090,420 B2  
(45) Date of Patent: Sep. 17, 2024

(54) SYSTEMS AND METHODS FOR RECOVERING AMINES AND THEIR DERIVATIVES FROM AQUEOUS MIXTURES

(71) Applicant: INV Nylon Chemicals Americas, LLC, Wilmington, DE (US)

(72) Inventors: Gary J. Smith, North Yorkshire (GB); Paul S. Pearlman, Thornton, PA (US); Gregory S. Kirby, Avondale, PA (US); Richard R. Rosin, Skokie, IL (US); Taylor Craig Schulz, Skokie, IL (US); Michael James Sargent, Cambridge (GB)

(73) Assignee: INV Nylon Chemicals Americas, LLC, Wilmington, DE (US)

( * ) Notice: Subject to any disclaimer, the term of this patent is extended or adjusted under 35 U.S.C. 154(b) by 53 days.

(21) Appl. No.: 16/572,899

(22) Filed: Sep. 17, 2019

(65) Prior Publication Data

US 2020/0108331 A1 Apr. 9, 2020

Related U.S. Application Data

(60) Provisional application No. 62/732,878, filed on Sep. 18, 2018.

(51) Int. Cl.
*B01D 11/02* (2006.01)
*B01D 11/04* (2006.01)
(Continued)

(52) U.S. Cl.
CPC ...... *B01D 11/0488* (2013.01); *B01D 15/3857* (2013.01); *B01J 39/05* (2017.01);
(Continued)

(58) Field of Classification Search
CPC ............ B01D 11/0488; B01D 15/3857; B01D 11/04; B01D 11/0492; B01D 15/00;
(Continued)

(56) References Cited

U.S. PATENT DOCUMENTS 2,739,986 A * 3/1956 Scudi .................. C07D 211/64  
564/511  
2,839,548 A 6/1958 Berther  
(Continued)

FOREIGN PATENT DOCUMENTS

CA 2404442 A1 10/2001  
CN 1257880 C 5/2006  
(Continued)

OTHER PUBLICATIONS

International Preliminary Report on Patentability issued in International Application No. PCT/US2016/026754, dated Oct. 19, 2017, 10 pages.
(Continued)

*Primary Examiner* — Joseph W Drodge

(57) ABSTRACT

The present disclosure generally relates to methods for the recovery of amines from aqueous mixtures. In particular, the disclosure relates to methods for separating amines from amine-containing aqueous mixtures by adjusting the pH of the aqueous mixture relative to the highest pKa value for the amines.

41 Claims, 13 Drawing Sheets

(51) Int. Cl.
    *B01D 15/38*     (2006.01)
    *B01J 39/05*     (2017.01)
    *C02F 1/66*     (2006.01)
    *C07C 209/84*     (2006.01)
    *C07C 209/86*     (2006.01)
    *C02F 103/36*     (2006.01)

(52) U.S. Cl.
    CPC .............. *C02F 1/66* (2013.01); *C07C 209/84* (2013.01); *C07C 209/86* (2013.01); *C02F 2103/36* (2013.01); *C02F 2305/14* (2013.01)

(58) Field of Classification Search
    CPC ............... B01D 17/02; B01D 17/0202; B01D 17/0208; B01D 17/0214; B01D 17/0217; B01D 37/00; B01D 61/14; B01D 61/16; B01D 61/20; B01D 21/00; B01D 21/02; B01D 21/10; B01D 21/26; C02F 1/66; C02F 2103/36; C02F 2305/14; C02F 1/001; C02F 1/42; C02F 9/00; C02F 2001/425; C02F 1/26; C02F 2001/007; C02F 2001/422; C02F 2001/427; B01J 39/05; B01J 39/00; B01J 39/04; B01J 39/08; B01J 47/00; B01J 47/014; B01J 49/00; B01J 49/05; B01J 49/06; B01J 49/50; B01J 49/53; B01J 49/70; B01J 41/00; B01J 47/02; C07C 209/84; C07C 209/86; C07C 67/48; C07C 67/56; C07C 67/58; C07C 67/62; C07C 209/82; C07C 209/90; C07C 211/09; C07C 211/10; C07C 211/11; C07C 211/12; C07C 213/10; C07C 227/38; C07C 227/40; C07C 227/44; C12P 13/001
    USPC ....... 210/259, 632, 634, 638, 639, 663, 669, 210/806; 435/128; 528/288; 562/554; 564/497, 498
    See application file for complete search history.

(56) References Cited

U.S. PATENT DOCUMENTS

| | | | |
|---|---|---|---|
| 2,840,606 A | 6/1958 | Miller | |
| 2,985,589 A | 5/1961 | Broughton et al. | |
| 3,017,435 A * | 1/1962 | Donald | C07C 209/02 564/485 |
| 3,069,465 A | 12/1962 | Monet | |
| 3,151,163 A | 9/1964 | Nussbaum | |
| 3,223,731 A | 12/1965 | Thorburn | |
| 3,393,233 A | 7/1968 | Richter | |
| 3,418,375 A * | 12/1968 | Schmitt | C07C 209/48 564/491 |
| 3,492,354 A | 1/1970 | Cywinski | |
| 3,578,432 A | 5/1971 | Stiles | |
| 3,696,107 A | 10/1972 | Neuzil | |
| 3,706,812 A | 12/1972 | Derosset et al. | |
| 3,761,533 A | 9/1973 | Otani et al. | |
| 4,091,039 A * | 5/1978 | Scheibel | C07C 29/095 562/606 |
| 4,263,145 A | 4/1981 | Wirth, Jr. | |
| 4,323,702 A | 4/1982 | Kawabata | |
| 4,333,740 A | 6/1982 | Piegnitz | |
| 4,461,649 A | 1/1984 | Neuzil et al. | |
| 4,483,980 A | 11/1984 | Neuzil | |
| 4,584,400 A | 4/1986 | Otani et al. | |
| 4,663,048 A | 5/1987 | Tanaka et al. | |
| 4,720,579 A | 1/1988 | Kulprathipanja | |
| 4,764,276 A | 8/1988 | Berry et al. | |
| 4,851,573 A | 7/1989 | Kulprathipanja | |
| 4,851,574 A | 7/1989 | Kulprathipanja | |
| 5,026,482 A | 6/1991 | Sircar | |
| 5,069,883 A | 12/1991 | Matonte | |
| 5,071,560 A | 12/1991 | McCulloch | |
| 5,266,694 A | 11/1993 | Moran, Jr. | |
| 5,279,744 A | 1/1994 | Itoh et al. | |
| 5,405,992 A | 4/1995 | Funk | |
| 5,663,424 A * | 9/1997 | Knofel | C07C 209/84 560/347 |
| 5,684,190 A | 11/1997 | Frechter et al. | |
| 5,750,791 A | 5/1998 | Davis et al. | |
| 5,751,406 A | 5/1998 | Nakazawa et al. | |
| 5,759,406 A | 6/1998 | Phelps et al. | |
| 5,779,814 A * | 7/1998 | Fellers, Sr. | C02F 5/12 134/20 |
| 6,087,494 A | 7/2000 | Thomissen | |
| 6,099,654 A | 8/2000 | Kaneko | |
| 6,146,534 A | 11/2000 | Grendze et al. | |
| 6,153,784 A * | 11/2000 | Kneuper | C07C 209/48 558/456 |
| 6,153,791 A | 11/2000 | Moore | |
| 6,284,904 B1 | 9/2001 | Ponnampalam | |
| 6,462,221 B1 | 10/2002 | Gabriel et al. | |
| 6,476,239 B1 | 11/2002 | Arumugam et al. | |
| 6,498,250 B2 | 12/2002 | Raets et al. | |
| 6,518,454 B1 | 2/2003 | Arumugam et al. | |
| 6,872,314 B2 | 3/2005 | Boyd et al. | |
| 6,979,402 B1 | 12/2005 | Sprague et al. | |
| 7,166,460 B2 | 1/2007 | Wilkins et al. | |
| 7,241,918 B1 | 7/2007 | Kulprathipanja | |
| 7,820,869 B2 | 10/2010 | Priegnitz et al. | |
| 8,729,298 B2 | 5/2014 | Zang et al. | |
| 9,061,267 B2 | 6/2015 | Gottshall et al. | |
| 9,315,443 B2 | 4/2016 | Erchardt et al. | |
| 9,233,906 B2 | 12/2016 | Gerberding et al. | |
| 9,878,321 B2 | 1/2018 | Kamionka et al. | |
| 10,255,542 B2 | 4/2019 | Smith et al. | |
| 10,343,084 B2 | 7/2019 | Pearlman et al. | |
| 2002/0035269 A1 | 3/2002 | Soper et al. | |
| 2003/0094416 A1 | 5/2003 | Heikkila et al. | |
| 2006/0058555 A1 | 3/2006 | Ostermaier | |
| 2007/0213415 A1 | 9/2007 | Sadis | |
| 2009/0036709 A1 | 2/2009 | Okada et al. | |
| 2009/0326308 A1 | 12/2009 | Kulprathipanja et al. | |
| 2010/0108610 A1 * | 5/2010 | Godhwani | B01J 49/06 210/670 |
| 2010/0189633 A1 * | 7/2010 | Schellen | B01J 8/0453 423/502 |
| 2010/0292429 A1 | 11/2010 | Volkert et al. | |
| 2011/0004018 A1 * | 1/2011 | Ito | C07C 209/84 564/138 |
| 2011/0160483 A1 | 6/2011 | Rezkallah | |
| 2012/0289742 A1 | 11/2012 | Gerberding et al. | |
| 2013/0030146 A1 | 1/2013 | Guit et al. | |
| 2013/0071893 A1 * | 3/2013 | Lynch | C12N 9/16 435/136 |
| 2013/0164801 A1 * | 6/2013 | Kang | C12P 7/62 435/135 |
| 2013/0183728 A1 | 7/2013 | Botes et al. | |
| 2013/0210090 A1 | 8/2013 | Pearlman et al. | |
| 2013/0217081 A1 | 8/2013 | Pearlman et al. | |
| 2013/0224807 A1 | 8/2013 | Pearlman et al. | |
| 2013/0245320 A1 * | 9/2013 | Yoshida | C07C 51/42 562/580 |
| 2014/0046023 A1 | 2/2014 | Gottshall et al. | |
| 2014/0051868 A1 | 2/2014 | Sokolov et al. | |
| 2014/0051888 A1 | 2/2014 | Dubay et al. | |
| 2014/0076805 A1 * | 3/2014 | Massingill | C07D 333/76 210/634 |
| 2014/0186902 A1 | 7/2014 | Botes et al. | |
| 2014/0193865 A1 | 7/2014 | Botes et al. | |
| 2014/0199737 A1 | 7/2014 | Botes et al. | |
| 2014/0242655 A1 | 8/2014 | Pearlman et al. | |
| 2014/0248673 A1 | 9/2014 | Botes et al. | |
| 2015/0004660 A1 | 1/2015 | Pearlman et al. | |
| 2016/0159723 A1 | 6/2016 | Smith et al. | |
| 2016/0289165 A1 * | 10/2016 | Murata | C07C 211/09 |
| 2016/0296926 A1 | 10/2016 | Kamionka et al. | |
| 2016/0297746 A1 * | 10/2016 | Smith | C07C 209/82 |
| 2016/0297747 A1 | 10/2016 | Conradie | |
| 2016/0326112 A1 * | 11/2016 | Brichant | C07D 209/20 |

(56) References Cited

U.S. PATENT DOCUMENTS

| | | | |
|---|---|---|---|
| 2017/0015616 A1* | 1/2017 | Gwak | C07C 209/84 |
| 2017/0349535 A1 | 12/2017 | Conradie | |
| 2017/0369913 A1* | 12/2017 | Suominen | C12Y 402/01001 |
| 2017/0369957 A1* | 12/2017 | Jansen | C12P 7/18 |
| 2018/0023103 A1* | 1/2018 | Foster | C12P 7/42 562/553 |
| 2018/0312887 A1* | 11/2018 | Lynch | C12P 7/16 |
| 2020/0108331 A1 | 4/2020 | Smith et al. | |

FOREIGN PATENT DOCUMENTS

| | | | |
|---|---|---|---|
| CN | 101823928 A | 9/2010 | |
| CN | 102206167 A | 10/2011 | |
| CN | 101423478 B | 5/2012 | |
| CN | 106367326 A | 2/2017 | |
| CN | 108276292 A | 7/2018 | |
| CN | 107056624 B | 4/2019 | |
| EP | 0324210 A1 | 7/1989 | |
| EP | 0415821 A1 | 3/1991 | |
| EP | 0664787 B1 | 6/1997 | |
| EP | 1106602 A1 | 6/2001 | |
| EP | 2345632 A1 | 7/2011 | |
| EP | 2591773 A2 | 5/2013 | |
| EP | 2591778 A1 | 5/2013 | |
| FR | 2103302 A5 | 4/1972 | |
| FR | 2651148 A1 | 3/1991 | |
| FR | 2651149 A1 | 3/1991 | |
| WO | 9008730 A1 | 8/1990 | |
| WO | 2013005046 A1 | 1/2013 | |
| WO | 2014113999 A1 | 7/2014 | |
| WO | 2016/106367 A1 | 6/2016 | |
| WO | 2016164748 A1 | 10/2016 | |
| WO | 2016164767 A1 | 10/2016 | |
| WO | 2016164798 A1 | 10/2016 | |

OTHER PUBLICATIONS

International Search Report and Written Opinion for PCT/US2016/026754, issue from European Patent, dated Jun. 17, 2016, p. 13.
Aminocaproic acid, Mar. 2006.
Gao et al. (Separation and Purification of γ-Aminobutyric Acid from Fermentation Broth by Flocculation and ChromatographicMethodologies, J. Agric. Food Chem. 2013, 61, 1914-1919). (Year: 2013).
Amberlite (Year: 2008).
International Preliminary Reporton Patentability issued in International Application No. PCT/US2016/026678, dated Oct. 19, 2017, 7 pages.
Kirk-Othmer, Encyclopedia of Chemical Technology, Fourth Edition, vol. 2, pp. 513-516 (1992).
Jansen, M.L et al., "Effect of pH and Concentration on Column Dynamics of Weak Electrolyte Ion Exchange," AICHE Journal, vol. 42, No. 7, pp. 1925-1937 (1996).
Helfferich, F.G., "Ion Exchange Equilibria of Amino Acids on Strong-Acid Resins: Theory," Reactive Polymers, vol. 12, pp. 95-100 (1990).
International Search Report and Written Opinion for International Application No. PCT/US2016/026678, dated Jun. 29, 2016, from the International Searching Authority, European Patent Office (12 pages).
Gonzalez-Pradas et al. (Removal of Aromatic Amines from Aqueous Solution by Activated Sepiolite, J. Chem. Tech. Biotechnol. 1990,47, 15-22) (Year: 1990).
Van Walsem, et al., "Simulated Moving Bed in tile Production of Lysine", Journal of Biotechnology, Elsevier Science Publishers, vol. 59, 1997, pp. 127-132.
International Search Report and Written Opinion received for PCT Patent Application No. PCT/US2016/026712, dated Jun. 21, 2016, 12 pages.
Buhlert, "Construction and Development of a New Single-Column Simulated Moving Bed System on the Laboratory Scale", Journal of Chromatography A, 1216, 2009, pp. 8778-8786.
CHE81:59758, Gamma-Amino Fatty Acid, available at <http://www.ebi.ac.ukichebi/searctlld.do?lebild=CHEBI :59758>, last modified on Nov. 7, 2016, 1 page.
Membrane Filtration Processes Technical Bulletin from TRISEP, available on <IItpsi/static1.squarespace.com/static/54e2b7 aee4b0902efd671 f90/tl580ff23b2e69cf6ad 153bd42/1477440060214/TB-025+Membrane+FiltrationProcesses+-+Dead-End>, Jun. 9, 2016, pp. 1-2.
Wikipedia, "Simulated Moving Bed", available at <https:!/en.wikipedla.org/wiki/Simulated_moving_bed>, last edited an May 5, 2017, 3 pages.
International Preliminary Reporton Patentability issued in International Application No. PCT/US2016/026712, dated Oct. 19, 2017, 10 pages.
Fritz, "Ion Chromatography", Analytical Chemistry, vol. 59, No. 4, 1987, p. 335A-344A.
Latterell, "Separation of Amines by Ligand Exchange_ Part 11", Analytica Chimica Acta, 32, 1965, pp. 101-109, 1965.
Anon, "Amine recovery using continuous ion-exchange", Research Disclosure, vol. 383, 1996, p. 206, 1996.
U.S. Non-Final Office Action issued in copending U.S. Appl. No. 15/094,770, filed Apr. 8, 2016, dated Jun. 15, 2017, 36 pages.
Notice of Allowance received in copending U.S. Appl. No. 15/094,770, filed Apr. 8, 2016, dated Nov. 30, 2016, 4 pages.
Notice of Allowance received in copending U.S. Appl. No. 15/094,770, filed Apr. 8, 2016, dated Oct. 28, 2016, 8 pages.
Non Final Rejection received in copending U.S. Appl. No. 15/094,770, filed Apr. 8, 2016, dated Mar. 13, 2018, 43 pages.
Notice of Allowance received in copending U.S. Appl. No. 15/094,770, filed Apr. 8, 2016, dated Jan. 3, 2019, 15 pages.
Walker et al. (Quantitative methods for amino acid analysis in biological fluids, Ann Clin Biochem; 32: 28-57 Published 1995) (Year: 1985).
International Search Report and Written Opinion for International Application No. PCT/US2019/051401, dated Dec. 11, 2019, p. 6.
Non-Final office action received for U.S. Appl. No. 15/491,018 dated Jul. 22, 2020, 24 pages.
Non-Final office action received for U.S. Appl. No. 15/847,854 dated Jul. 14, 2020, 18 pages.
U.S. Appl. No. 62/144,884, filed Apr. 18, 2015, 18 pages.

* cited by examiner

SYSTEMS AND METHODS FOR RECOVERING AMINES AND THEIR DERIVATIVES FROM AQUEOUS MIXTURES

RELATED APPLICATIONS

This application claims priority to U.S. Provisional Patent Application No. 62/732,878, filed Sep. 18, 2018, the entire contents of which are incorporated herein by reference.

FIELD

The present disclosure generally relates to methods for the recovery of amines from aqueous mixtures. In particular, the present disclosure relates to methods for separating amines from amine-containing aqueous mixtures by increasing the pH of the aqueous mixture to at least one pH unit above the highest pKa for the amine. A resulting amine-rich layer can be formed and separated, or the amine can be extracted.

BACKGROUND

Amines have a multitude of industrial and medicinal uses. Diamines are typically used as monomers in the synthesis of a variety of materials such as polyamide resins and fibers. Some examples of diamines include C4-C7 diamines, such as 1,4-butanediamine (putrescine/1,4-diaminobutane), 1,5-pentanediamine (cadaverine/1,5-diaminopentane/pentamethylenediamine (PMD)), 1,6-hexanediamine (1, 6-diaminohexane/hexamethylenediamine (HMD)) or 1,7-heptanediamine (1,7-diaminoheptane/heptamethylenediamine). For instance, the diamine hexamethylenediamine (HMD) is a chemical intermediate used in the production of nylon 6,6 via a condensation reaction with adipic acid. HMD is also used in the production of epoxy resins as well as the production of monomers for polyurethanes.

Often in chemical processes, it is necessary to separate useful amines from aqueous mixtures, which sometimes also include acid and/or salt impurities. The amine can be chosen, for example, from diamines. In biological processes such as fermentation, it may be necessary to separate amines from acid impurities, for example separation of cadaverine from lysine or separation of HMD from adipic acid or aminocaproic acid.

Biological processes, however, frequently suffer from several limitations including 1) a relatively small range of products; 2) low yields, titers, and productivities; and 3) difficulty recovering and purifying products from aqueous mixtures. In particular, during the recovery step, techniques such as distillation, decantation, extraction, pervaporation, and chromatography have been employed. These methods, however, may be energy intensive, expensive to operate, and impractical or uneconomical for the recovery and purification of materials from, for example, a fermentation broth. Therefore, the need exists for improved methods of separating amines from aqueous mixtures that are efficient and inexpensive.

In addition, some amines are temperature sensitive and may degrade or dimerize/trimerize especially in the presence of impurities and contaminants when exposed to temperatures encountered in common separation processes, such as distillation, pervaporation, or evaporation. This can be especially true given the potential for higher temperature conditions at certain points, for example at the column base or reboiler of a distillation column. Also, concentration of an amine in aqueous mixtures containing a strong base via distillation can lead to unwanted side reactions resulting in byproducts, especially as the amine concentration increases and the still temperature increases. Thus, a process that would avoid exposing the amine to potential degradation conditions would be desirable.

Commercial applications of amines (including monoamines and polyamines) may require them to be of very high purity with low quantities of impurities. Accordingly, it would be beneficial to be able to separate amines (including monoamines and polyamines) produced in, for example, a biological process in a simple, efficient, and low-cost way. It would be particularly advantageous to efficiently separate insoluble non-valent amines from impurities containing acidic groups, for example, to separate cadaverine from lysine or HMD from adipic acid or aminocaproic acid.

In addition, waste and/or recycled nylon polymer containing diamines such as, nylon-6,6, nylon-4,10, nylon-6,10, nylon-4,6, nylon-5,6 and nylon-6,12 can be recycled by depolymerizing the polymer via acid or base hydrolysis. Value can be extracted from this waste material by recovering its individual components and then recycling these individual components to make additional nylon polymer. For example, U.S. Pat. No. 3,069,465 provides a method for recovery of adipic acid and HMD from nylon using crystallization and neutralization. However, the method maintains relatively high water and sodium concentrations. It would be beneficial to sustain lower water and sodium concentrations in separating the amine. In addition, a simpler method with fewer steps and less expense would be highly desirable.

Relatedly, it would also be beneficial to recover diamines in aqueous effluent streams with low diamine concentration from nylon polymer polymerization processes, for example, to recover HMD in dilute HMD aqueous effluent streams formed during nylon-6,6 polymerization.

Weak bases such as amines dissolve in water by dissociating to form positively charged ammonium species. The pKa value for a given amine reflects the ratio of the ionized species to the non-ionized species at equilibrium in a solution of the amine in water without introduction of additional acid or bases. At the pKa, the concentration of ammonium species and the concentration of non-ion free-amine species are equal. For a monoamine such as hexylamine, there is one pKa value reflecting the equilibrium concentrations of the hexylamine (HA) and the hexylammonium (HA+) salt. For multivalent amines such as diamines and triamines, the compounds have multiple pKas representing the species equilibrium for each of the potential species pairs. For a diamine such as HMD, there are two pKa values. The lower pKa value represents the equilibrium between the divalent (HMD+2) and the monovalent (HMD+1) species. The higher pKa value represents the equilibrium concentration between the monovalent (HMD+1) species and the nonvalent free amine HMD. The higher pKa value is represented by the greatest numerical value. For a diamine having a lower pka value and a higher pKa value, the higher pKa value is clearly taken to be the highest pKa according to the present invention. If the pH of the aqueous mixture is equal to the higher pKa 50% of the HMD will be present in the nonvalent free amine HMD form. As the pH is increased by addition of base, the proportion of HMD in the free amine form will increase. For a triamine such as diethylenetriamine, there are three pKa values. The highest pKa value is the pKa value with the greatest numerical value.

SUMMARY

In some embodiments, the present disclosure relates to a method of separating at least one amine from an aqueous mixture, comprising providing an aqueous mixture comprising water and the at least one amine; increasing the pH of the aqueous mixture to at least one pH unit above the highest pKa for the amine; forming an aqueous layer and an amine-rich layer, wherein the amine-rich layer comprises the at least one amine; and separating the amine-rich layer from the aqueous layer. The resulting amine may then be recovered from the separated amine-rich layer. In other embodiments, the present disclosure relates to a method of separating at least one amine that does not comprise an acidic group such as a carboxylic acid, sulfonic acid, or phosphonic acid, from an aqueous mixture, the method involves providing an aqueous mixture comprising water and the at least one amine having a highest pKa value; increasing the pH of the aqueous mixture to at least 1.0 pH unit above the highest pKa value; forming an aqueous layer and an amine-rich layer containing the at least one amine; and separating the amine-rich layer from the aqueous layer. In embodiments, the at least one amine can be a monoamine, a diamine, or a triamine. For example, the at least one amine might be 1,4-diaminobutane, pentamethylenediamine, hexamethylenediamine, heptamethylenediamine, hexyl amine, nonyl amine, aminonitrile, diethylenetriamine, or combinations thereof. In embodiments, the aqueous mixture can contain the amine in a concentration less than 20 wt. %, less than 15 wt. %, or less than 10 wt. %. After the amine-rich layer is formed, it may have an amine concentration layer of more than 30 wt. % in some embodiments. Other embodiments can involve increasing the pH of the aqueous mixture to at least 2.0 pH units above the highest pKa value for the at least one amine.

The present disclosure can also relate to the additional step of changing the density difference between the amine-rich layer and the aqueous layer to at least 0.1 g/L, at least 0.2 g/L, or at least 0.3 g/L. In some embodiments, this can be performed simultaneously with the pH increase. This can be done, for example, by the addition of a concentrated strong basic alkaline solution or solid strong bases such as sodium or potassium hydroxide to the aqueous mixture to simultaneously raise the pH and achieve the required density differences. Other embodiments involve performing the density change and pH increase consecutively. This can be done, for example, by first raising the pH to the desired level and subsequently adding one or more inorganic salts, such as sodium salts, calcium, or potassium salts to the aqueous mixture or layer until the aqueous layer achieves the desired density.

In some embodiments, the separation of the amine-rich layer from the mixture can comprise extraction or physical separation, e.g., forming two immiscible aqueous layers having different densities (one being an amine-rich layer). In some embodiments, the organic solvent can dissolve the at least one amine. Extraction can comprise, in some embodiments, contacting the aqueous mixture with an organic solvent that is at least partially immiscible with water. The organic solvent can be, in some embodiments, In some embodiments, this can be done via one or mixer settler systems. The extraction may be a continuous process.

In some embodiments, the present disclosure relates to aqueous mixtures derived from an ion exchange elution, hydrolyzed polyamide polymer (such as nylon-6,6, nylon-4,6, nylon-4,10, nylon-5,6, nylon-6,10, or nylon-6,12, for example), fermentation broth, dilute stream from an amine production process, or dilute aqueous effluent stream from polyamide polymerization In some embodiments the step in increasing the pH of the aqueous mixture to 1.0 pH unit above the highest pKa value for the at least one amine results in the formation of a non-valent species of the amine in a concentration of greater than 90 wt. %. In other embodiments, where the pH of the aqueous mixture is raised to 2.0 pH units above the highest pKa value for the at least one amine, a non-valent species of the amine can be formed in a concentration of greater than 99 wt. %.

Other embodiments of the present disclosure relate to methods of reducing the salt to amine ratio in an aqueous mixture comprising at least one amine comprising the steps of: increasing the pH of the aqueous mixture to a pH where a non-valent species of the least one amine is formed in an amount greater than 90 wt. %, or in some cases greater than 98 wt. %, of the total amount of the at least one amine; forming an amine-rich layer and an aqueous layer, wherein the amine-rich layer is immiscible in the aqueous layer; and separating said amine-rich layer from the aqueous layer. In embodiments, the aforementioned salt to amine weight ratio can be reduced by 85% or more, or 75% or more. The pH might be increased to 12.5 or more in some embodiments.

Embodiments of the present disclosure can also relate to methods of separating amines from aqueous mixtures containing acidic species comprising the steps of: increasing the pH of an aqueous mixture comprising acidic species and at least one amine to a pH where (1) a non-valent species of the least one amine is formed in an amount greater than 90 wt. % of the total amount of the at least one amine, and (2) at least a portion of the non-valent species of the at least one amine is not soluble in the aqueous mixture; and separating said amine-rich portion from the mixture. The acidic species might comprise carboxylic acids or amines containing acidic moieties in some embodiments. In other embodiments, the acid species may comprise an amino-acid, α-amino acid or an Ω-amino acid. Thus, for example, the at least amine might comprise a diamine and the acid species might comprise an amino acid in some specific embodiments.

In still other embodiments, the present disclosure can related to methods of recovering at least one amine from an aqueous mixture comprising: contacting an ion exchange resin with the aqueous mixture comprising the at least one amine to produce a resin containing at least a portion of the at least one amine; treating the resin containing the at least a portion of the at least one amine with a base eluent to produce an amine-containing elution; adjusting the pH of the amine-containing elution to at least 1.0 pH unit above the highest pKa value for the at least one amine; and recovering the at least one amine. This recovery step might involve, in some embodiments, physically separating the amine containing elution after adjusting its pH into an amine-rich layer and an amine depleted aqueous layer, and removing the amine-rich layer. Some embodiments also involve the addition of a salt to the eluent to improve the physically separating the amine containing elution after adjusting its pH into an amine-rich layer and an amine depleted aqueous layer, and removing the amine-rich layer. In other embodiments, the recovery step comprises extracting the amine containing elution after adjusting its pH with an organic solvent to produce an amine containing organic layer comprising at least a portion of the at least one amine and an amine depleted aqueous layer. At least a portion of the amine depleted layer might be recycled to the base eluent and treated, in some embodiments. Other embodiments can involve recycling the amine-depleted aqueous layer to the base eluent. An ion exchange resin can be used for conducting the contacting step in some embodiments. Some embodiments involve a settler or an extractor for conducting the recovery step.

BRIEF DESCRIPTION OF THE DRAWINGS

The present disclosure will be better understood in view of the appended non-limiting figures, in which.

DETAILED DESCRIPTION

Figure 1:
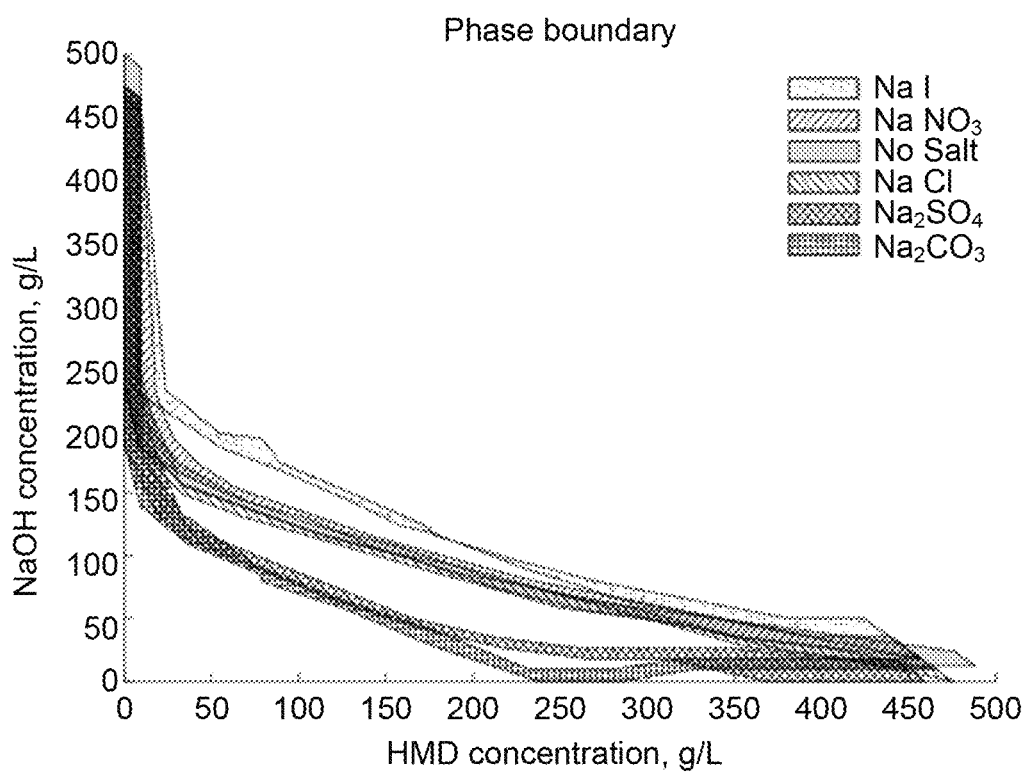
FIG. 1 shows a phase boundary diagram for an HMD and NaOH solution to which various sodium salts have been added. The patterned areas represent the phase boundary lines between the single-phase region (below the line) and the two-phase (biphasic) region (above the line). The effect on the phase boundary obtained by the addition of various sodium salts is demonstrated by comparison to the phase boundary of the solution with no additional salt.

The present disclosure relates to methods for concentrating amines from aqueous mixtures that are efficient and inexpensive. The present methods advantageously do not have large energy and capital requirements, especially when compared with standard separation or concentration procedures such as distillation, pervaporation and chromatography. Further, the present disclosure offers the benefit of not exposing such amine-containing streams to potential degradation conditions, thereby preserving and improving the amine content and recoverable product yield. As a result, the present disclosures provide highly desirable methods from the standpoint of improved equipment productivity and reduced processing cost.

In some embodiments, for example, the present disclosure relates to methods of separating at least one amine from an aqueous mixture. In some aspects, the method comprises the step of providing an aqueous mixture comprising water and the at least one amine. The pH of the aqueous mixture is then increased to at least 1.0 pH unit above the highest pKa value of the at least one amine, thereby forming an aqueous layer and an amine-rich layer, wherein the amine-rich layer comprises the at least one amine. In some aspects, the method also includes the step of separating the amine-rich layer from the aqueous layer. The resulting amine may then be desirably recovered from the separated amine-rich layer.

Additionally, in some aspects, the present disclosure relates to methods for increasing the amine concentration and reducing the salt to amine concentration ratio. The overall reduction in the salt concentration is important, namely both the cation and anion, for example, a reduction in both sodium cations and chloride anions is important where, for example, sodium chloride is used. This is especially important for certain processes. For example, in chemical processes that involve ion-exchange units, reduction of salts resulting from an elution step is especially important when ammonia cannot be used as a base. Instead, sodium hydroxide or potassium hydroxide are typically used, thereby contributing to a high sodium/potassium content of the resulting process streams. High sodium or potassium salts (or other salt) to HMD ratios may cause problems when purifying the resulting process streams, especially under distillation, as the salts could lead to by-product formation. However, the present disclosure has the additional benefit of reducing the salt to amine ratio in the amine-containing stream or layer. This benefit is achieved by preferentially partitioning the salts into the aqueous layer and away from the amine-rich layer during separation.

The disclosure also provides methods for separating at least one amine from a dilute aqueous mixture by concentrating the amine and subsequently separating the amine from the dilute aqueous mixture. In this context, the term "dilute aqueous mixture" refers to an aqueous mixture wherein the concentration of amine is less than 20%. The dilute aqueous mixture may also contain water soluble impurities which beneficially remain with the aqueous layer after separation of the amine(s).

After intensive studies, it has now been surprisingly and unexpectedly discovered that amines can be recovered from aqueous mixtures by adjusting, e.g., increasing, the pH of the aqueous mixture relative to the highest pKa value for the amine. The term "pKa" refers to the acid dissociation constant for the amine. The pKa value for a given amine reflects the ratio of the ionized species to the non-ionized species at equilibrium in a solution of the amine in water without introduction of an additional acid or bases. At the pKa, the concentration of ammonium species and the concentration of non-ion free-amine species are equal. For a monoamine such as hexylamine, there is one pKa value reflecting the equilibrium concentrations of the hexylamine (HA) and the hexylammonium (HA+) salt. For multivalent amines such as diamines and triamines, the compounds have multiple pKas representing the species equilibrium for each of the potential species pairs. For a diamine such as HMD, there are two pKa values. The lower pKa value represents the equilibrium between the divalent (HMD+2) and the monovalent (HMD+1) species. The higher pKa value represents the equilibrium concentration between the monovalent (HMD+1) species and the nonvalent free amine HMD. The higher pKa value is represented by the largest numerical value. For a diamine having a lower pka value and a higher pKa value, the higher pKa value is clearly taken to be the highest pKa according to the present disclosure. If the pH of the aqueous mixture is equal to the higher pKa 50% of the HMD will be present in the nonvalent free amine HMD form. As the pH is increased by addition of base, the proportion of HMD in the free amine form will increase. For a triamine such as diethylenetriamine, there are three pKa values. The highest pKa value is the pKa value with the greatest numerical value.

In some aspects, the amine can be concentrated by adjusting the pH of the amine-containing aqueous mixture to at least 1.0 pH unit above the highest pKa value for the amine. Further, in some aspects, the amine can be concentrated by adjusting, e.g., increasing the pH of the amine-containing aqueous mixture to at least 1.0 pH unit above the highest pKa value for the amine and preferably at least 2.0 pH units above the highest pKa value for the amine such that substantially all (for example, at least 90%, at least 95% or at least 99%) of the amine species are present in the form of non-valent species. When the pH is adjusted to be at least 1.0 pH units above the highest pKa value, at least about 90% of the amine species are non-valent. When the pH is adjusted to be at least 2.0 pH units above the highest pKa value, at least about 99% of the amine species are non-valent. Without being bound by theory, these non-valent species may tend to be less polar and/or exhibit reduced hydrogen bonding, thereby reducing solubility of the amine species in the high pH aqueous mixture and thereby allowing the aqueous mixture to form separate amine-rich and aqueous layers, which may be advantageously separated, for example, by phase separation or via extraction. The amine-rich layer can have an amine concentration of more than 30 wt. %.

In some aspects, the amine can be at least one diamine or monoamine or triamine.

For example, diamines, optionally C3-C10 or C4-C7 diamines, such as hexamethylenediamine (HMD) and pentamethylenediamine (PMD), can be separated and recovered. In some embodiments, the amine, e.g., monoamine or diamine, can have a carbon chain length of from C1 to C10, e.g., from C2 to C9, from C3 to C8, or from C4 to C7.

In some aspects, the amines can be recovered from dilute aqueous mixtures from a variety of sources including but not limited to ion exchange chromatography elutions, recycled hydrolyzed polyamides such as nylon 5,6, nylon 6,6, nylon 6,10 and nylon 6,12 mixtures, fermentation broths, and dilute aqueous effluent streams from nylon 5,6, nylon 6,6, nylon 6,10 and nylon 6,12 polymerization or mixtures containing acid impurities.

In some aspects, salts may be added to the aqueous mixtures to improve the phase separation. The addition of salts may result in a clean concentrated secondary layer of amine (amine-rich layer) which can be physically separated from the aqueous layer containing water and water-soluble impurities (e.g., salts and acids). The addition of salts can desirably increase the density of the aqueous mixture relative to the amine-rich layer, thereby improving the separation. In some embodiments, the steps of increasing the pH and the density of the aqueous mixture and/or resulting aqueous layer may occur simultaneously. In other embodiments, the steps of increasing the pH and the density may occur consecutively, in either sequence.

In some aspects, after the pH is increased to at least 1.0 pH unit above the highest pKa, the aqueous mixture may be mixed with an organic solvent such as isopropanol, n-butanol, methylene chloride, or toluene which may extract the free amine from the aqueous mixture to form a separable organic layer that contains the amine. In some aspects, this mixing can occur in a continuous extraction. In some aspects, this mixing can occur via one or more mixer settler systems. In other embodiments the organic solvent can be removed via evaporation or other methods to give a predominantly amine rich stream.

Figure 6:
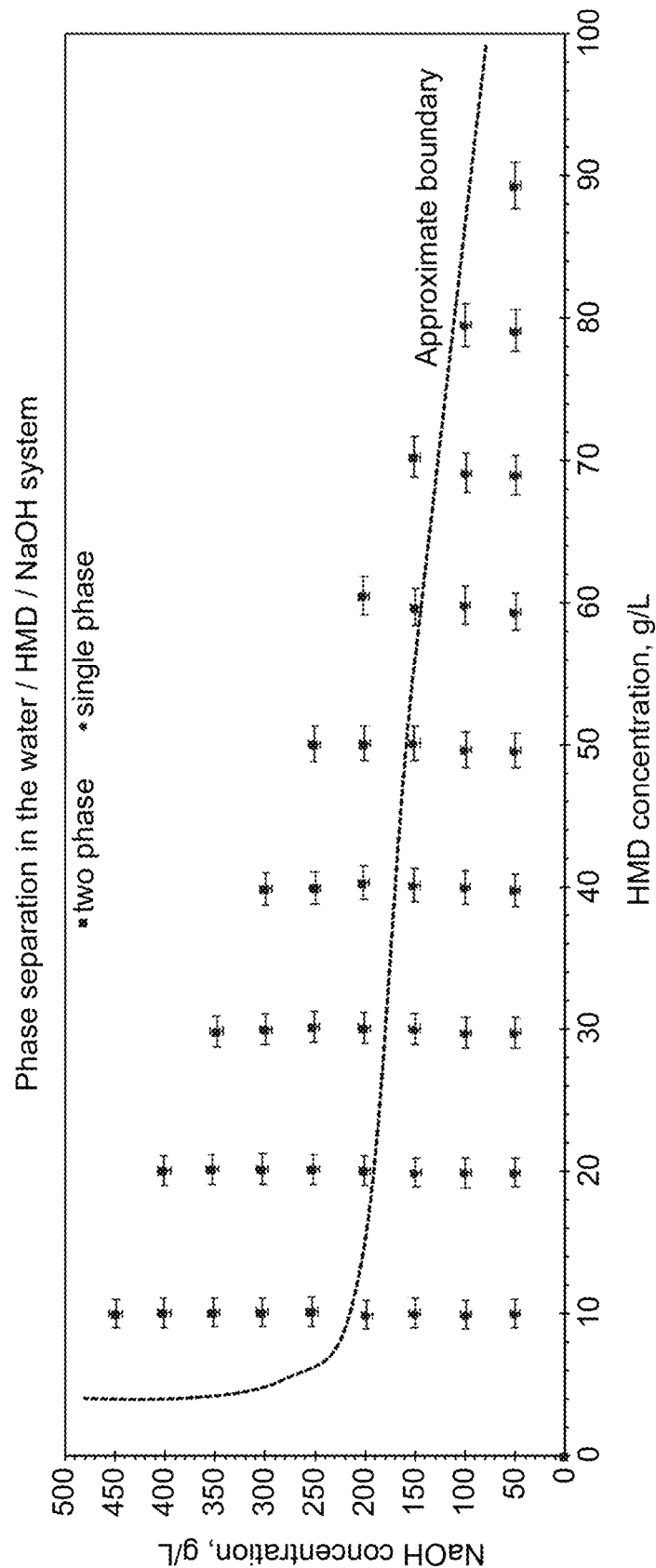
FIG. 6 shows a phase diagram. The area beneath the phase separation boundary line is represented as the single phase region whilst the area above the phase separation boundary line is represented as the two-phase (biphasic) region. The dashed line represents the phase separation boundary line. Separation is improved when the two-phase region is expanded by lowering the phase separation boundary line.

In some embodiments, the biphasic system of the present invention comprises two phases, namely an aqueous layer and an amine-rich layer, wherein the amine-rich layer comprises at least one diamine being separated. The aqueous layer is amine-depleted. The two phases can be aqueous-aqueous (e.g., amine-rich and amine-depleted) or aqueous-organic (e.g., aqueous and solvent for cases when solvent extraction is used). The aqueous layer (amine depleted) and the amine-rich layer can be represented on a phase diagram, for example, FIG. 6, with separation between the two layers drawn on the diagram as a phase separation boundary line. In some embodiments, the separation boundary line is lowered, thereby improving separation, for example, when inorganic salts are added, in particular, sodium sulphate or sodium carbonate.

Aqueous Mixtures

The methods in the present disclosure involve separation of at least one amine from an aqueous mixture. As used herein, the term "aqueous mixture" refers to any liquid mixture, solution, emulsion or suspension, in which water is the major component. By "major component," it is meant that the component of greatest concentration by weight. In some aspects, for example, the aqueous mixture comprises water in an amount greater than 50 wt. %, e.g., greater than 60 wt. % or greater than 75 wt. %. In other embodiments, the aqueous mixtures may be dilute. e.g., comprising less than 20 wt. % amine, less than 10 wt. % amine or less than 5 wt. % amine or less than 2% wt. % amine.

The methods of the present disclosure can be used in a variety of contexts, such as to increase the concentration or separate an amine stream from an ion exchange elution or to separate an amine from recycled hydrolyzed polyamides such as nylon 5,6, nylon 6,6, nylon 6,10 and nylon 6,12. In other contexts, the methods may be used to reduce amine content of dilute aqueous mixtures, e.g., dilute aqueous effluent streams, from polyamide polymerization processes such as nylon 5,6, nylon 6,6, nylon 6,10 and nylon 6,12 polymerization processes, or separating amines from acidic species including amino acids, e.g., separating PMD from a fermentation broth containing amino acids such as lysine.

Further non-limiting examples of amine-containing aqueous mixtures, e.g., process streams, according to the present disclosure may include: by-product purge streams from amine production facilities, amine refining facilities, processes that use amine-containing streams for component separations and purifications (gas absorption, extraction, etc.), aqueous streams generated in the condensation polymerization production facilities such as polyamides (or nylon) and co-polyamides production, fermentation processes, bio-production systems, dyes/color processes, pharmaceutical processes, and the like. Amine-containing gaseous streams may also be brought in contact with an aqueous medium to transfer the amine components into the aqueous medium, which may be used as a feed, according to the present disclosure.

The aqueous mixture may also contain water soluble impurities such as acids and/or salts, which can beneficially remain with the aqueous mixture after separation of the amine.

The process according to the present disclosure may be integrated with several industrial chemical unit operations such as decanters, mixer-settlers, evaporators, distillative separations, extractive separations, crystallizers, filtration, cyclone separators, gas-liquid separators, chemical reactors, physi-sorption and/or chemi-sorption units, among others. A person or ordinary skill in the art will appreciate that the amine concentration increase operation according to the present disclosure can be integrated into a chemical flow-sheet with material and energy balance closures within the flow sheets.

Amine

The at least one amine separated from the aqueous mixture according to the present disclosure can be a single amine or a plurality of amines. In embodiments, the at least one amine does not contain an acidic group ("non-acidic amine").

In other embodiments, however, the aqueous mixture may comprise an acidic amine in combination with the at least one amine that does not comprise an acidic group. A non-limiting list of exemplary acidic groups include, for example, carboxylic acid, sulfonic acid, or phosphonic acid groups.

In embodiments, the amine can be at least one diamine. In other embodiments, the amine can be at least one monoamine. In embodiments, the amine can be at least one diamine or monoamine. For example, diamines such as hexamethylenediamine (HMD) and pentamethylenediamine (PMD) can be advantageously separated and recovered. In embodiments, the amine can be at least one monoamine with limited aqueous solubility at high pH.

An amine is typically a compound or functional group that contains at least one basic nitrogen atom with a lone electron pair. It can be a primary (R—NH2), a secondary (R',R"—NH) or a tertiary amine (R',R",R'"—N), where R represent an alkyl or other organic substituent. For primary amines, the R represents an alkyl group, in which the NH2-group is placed at the end of the alkane chain. A monoamine is an amine with one amine group. A diamine is an amine with two amine groups.

In some embodiments, in addition to the amine functionality, the amine can contain at least one carbon chain length of from 1 to 10 carbon atoms (C1 to C10), e.g., from C2 to C9, from C3 to C8, or from C4 to C7.

Further non-limiting examples of amines that can be separated according to the methods disclosed herein include: Pyrrolidine, Dibutylamine, Piperidine, Diethylamine, Butylamine, Triethylamine, Dimethylamine, 2-Heptylamine, Propylamine, tert-Butylamine, Ethylamine, Heptylamine, Cyclohexylamine, Octylamine, Nonylamine, Decylamine, Pentylamine, Undecylamine, Dodecylamine, (Tridecyl) amine, Hexadecylamine, Tetradecylamine, Butylamine, Pentadecylamine, Octadecylamine, 2-Propanamine, sec-Butylamine, Methylamine, Hexylamine, iso-Butylamine, Trimethylamine, Allylamine, 2,4,6-trimethylpyridine, 2-Methylpyridine, 4-Methylpyridine, 2-Ethylpyridine, Acridine, Benzo[c]quinolone, 3-Methylpyridine, Isoquinoline, Pyridine, 2-Benzylpyridine, p-Toluidine, Quinoline, m-Toluidine, Aniline, o-Toluidine, 4-Aminobiphenyl, n-Allylaniline, 1,2-Propandiamine, 1,3-Propandiamine, 1,4-butanediamine, 1,5-pentanediamine, 1,6-hexanediamine, Cis-1,2,cyclohexanedimaine, Trans-1,2,cyclohexanedimaine, p-Benzidine, 1,2-diaminobenzene, 1,3-diaminobenzene, 1,4-diaminobenzene. In some aspects, the methods of the present disclosure include separating a plurality of amines from an aqueous mixture, optionally separating two or more of the above-listed exemplary amines from an aqueous mixture.

Amine Separation

The methods for amine separation and recovery involve adjusting, preferably increasing, the pH of the aqueous mixture relative to the highest pKa value for the amine. Table 1 shows pKa values for representative monoamines and Table 2 shows higher pKa values for representative diamines. The higher pKa value is represented by the greatest numerical value.

In embodiments, the amine can be concentrated by adjusting, e.g., increasing, the pH of the amine-containing aqueous mixture to above the highest pKa value for the amine. In some embodiments, the amines can be concentrated by adjusting, e.g., increasing, the pH of the amine-containing aqueous mixture to at least 1.0 pH unit above the highest pKa value for the amine, e.g., at least 1.2 pH units above the highest pKa value for the amine, at least 1.3 pH units above the highest pKa value for the amine, at least 1.4 pH units above the highest pKa value for the amine, at least 1.5 pH units above the highest pKa value for the amine, at least 1.6 pH units above the highest pKa value for the amine, at least 1.7 pH units above the highest pKa value for the amine, or at least 1.8 pH units above the highest pKa value for the amine. The highest pKa value for the amine refers to the greatest pKa value at the conditions employed (temperature, etc.). In the case where the amine is polyprotic, it is again the largest of the multiple pKas at the conditions employed. Some preferred embodiments involve adjusting, e.g., increasing, the pH of the amine-containing aqueous mixture to at least 2 pH units (or pKa units) above the highest pKa value for the amine, e.g., at least 2.1 pH units above the highest pKa value for the amine, at least 2.2 pH units above the highest pKa value for the amine, at least 2.3 pH units above the highest pKa value for the amine, at least 2.4 pH units above the highest pKa value for the amine, or at least 2.5 pH units above the highest pKa value for the amine. In the case of adjusting, e.g., increasing, to at least 2.0 pH units above the highest pKa value for the amine in embodiments substantially all of the amine species can be non-valent species (after the adjusting/increasing step). For example, 95% by weight or greater of the amine species can be non-valent species, 97% by weight or greater of the amine species can be non-valent species, 98% by weight or greater of the amine species can be non-valent species, or 99% by weight or greater of the amine species can be non-valent species after the adjusting or increasing pH step. Similarly, when the pH is adjusted, e.g., increased, to be at least 1.0 pH above the highest pKa value, most of the amine species can be non-valent species. For example, 90% by weight or greater of the amine species can be non-valent species, 95% by weight or greater of the amine species can be non-valent species, or 99% by weight or greater of the amine species can be non-valent species after the adjusting or increasing step.

The pH of the aqueous mixture can be adjusted, e.g., increased, by means known in the art. For example, the pH can be adjusted upwards by the addition of at least one base. In embodiments, the pH can be adjusted by the addition of a strong base, meaning a base that completely dissociates in an aqueous solution. In other embodiments, the pH can be adjusted by the addition of a neutral or weak base, meaning a base that only partially dissociates in water. In embodiments, the base can be a monoacidic base. In other embodiments, the base can be a diacidic base. In further embodiments, the base can be a triacidic base.

Without being bound by theory, it is believed that the species distribution is altered as the pH of the mixture changes, e.g., increases, resulting in desirable component (in)solubilities that allow for separation of the amine-rich layer from an aqueous layer. At lower pH, divalent species of amine may be formed whereas at higher pH, non-valent species of amine may be formed, which preferably exhibit reduced water solubility relative to the valent species. At a pH in between a low pH and a high pH, the monovalent species may be formed. Non-valent species preferably exhibit low solubility in the high pH aqueous mixture, allowing the amines to be separated, for example, by phase separation (e.g., forming two immiscible aqueous layers having different densities (one being an amine-rich layer) or via extraction, wherein the aqueous mixture may be mixed with an organic solvent such as isopropanol, n-butanol, methylene chloride, or toluene which may extract the free amine from the aqueous mixture to form a separable organic layer that contains the amine. In some aspects, this mixing can occur in a continuous extraction. In some aspects, this mixing can occur via one or more mixer settler systems. In other embodiments the organic solvent can be removed via evaporation or other methods to give a predominantly amine rich stream.

Figure 10:
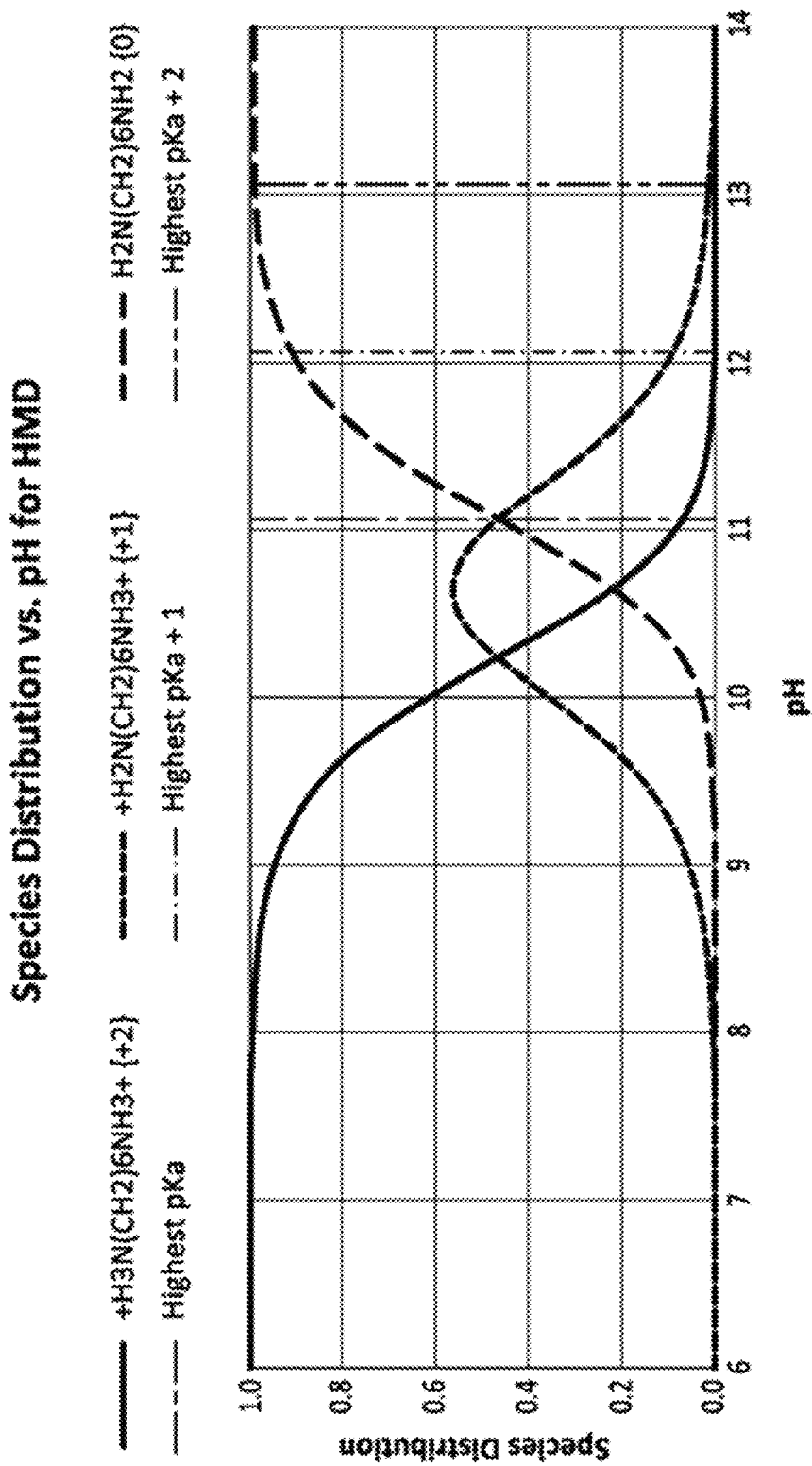
FIGS. 10A and 10B shows the species distribution of HMD and hexylamine at varying pH to help illustrate embodiments of the present disclosure.

As an example, FIG. 10A shows a species distribution for the amine hexamethylenediamine (HMD) as the pH of a dilute aqueous mixture is altered, according to the Henderson-Hasselbalch equation. At a lower pH, the divalent HMD species is predominantly present whereas at a higher pH, the non-valent HMD species predominates. At a pH of around pH 9-13, e.g., pH 10.4-11, the monovalent HMD species is also present. At pH of 1.0 pH unit above the highest pKa value (pH 12), approximately 90% of the HMD is in the non-valent form while at 2.0 pH units above the highest pKa value (pH 13), approximately 99% of the HMD is in the non-valent form. The non-protonated non-valent species is less soluble in water and hence at a high pH (e.g., more than pH 11, more than pH 12 or more than pH 13), where non-valent HMD species predominates over the other amine species, the solubility of the HMD decreases. Without being bound by theory, in embodiments combining increased pH with increased density of the aqueous mixture, this decrease in solubility in combination with the increase in density of the aqueous mixture promotes the separation of the amine, e.g., HMD, from the aqueous mixture. Thus, in preferred embodiments, the pH of the system should be high enough above the highest pKa value for HMD to form mostly or almost exclusively the non-valent HMD species.

In some aspects, after the pH of the aqueous mixture has been adjusted to above 12.0, e.g., above 12.3, above 12.5, above 12.8, above 13.0, above 13.1, above 13.3, or above 13.5, the amine, e.g., HMD, can be separated from the resulting aqueous layer by phase separation or extraction with an organic solvent such as isopropanol, n-butanol, toluene or methylene chloride, for example.

As a further example, FIG. 10B shows a species distribution for the monoamine hexylamine as the pH of a dilute aqueous mixture is altered, according to the Henderson-Hasselbalch equation. At a lower pH, the monovalent hexylamine species is predominantly present whereas at a higher pH, the non-valent hexylamine species predominates. For hexylamine, the highest pKa value is 10.5. At a pH of 1.0 pH unit above the highest pKa value (pH 11.5), approximately 90% of the hexylamine is in the non-valent form while at 2.0 pH units above the highest pKa value (pH12.5), approximately 99% of the hexylamine is in the non-valent form. The non-protonated non-valent species is less soluble in water and hence at a high pH (e.g., more than pH 11, more than pH 12 or more than pH 13), where non-valent hexylamine species predominates over the other amine species, the solubility of the hexylamine decreases. Without being bound by theory, in embodiments combining increased pH with increased density of the aqueous mixture, this decrease in solubility in combination with the increase in density of the aqueous mixture promotes the separation of the amine, e.g., hexylamine, from the aqueous mixture. Thus, in preferred embodiments, the pH of the system should be high enough above the highest pKa value for hexylamine to form mostly or almost exclusively the non-valent hexylamine species.

In some aspects, after the pH of the aqueous mixture has been adjusted to above 12.0, e.g., above 12.3, above 12.5, above 12.8, above 13.0, above 13.1, above 13.3, or above 13.5, the amine, e.g., hexylamine, can be separated from the resulting aqueous layer by phase separation or extraction with an organic solvent such as isopropanol, n-butanol, toluene or methylene chloride, for example.

Although different amines have different highest pKa values, the method operates similarly to the above examples of HMD and hexylamine for different amines. Table 1 below shows the pKa value for representative monoamines. Where there is a single pKa value, as for monoamines, this pKa value is taken to be the highest pKa value in accordance with the present disclosure. Table 2 below, shows the higher pKa and lower pKa values for representative diamines. Where there is a higher pKa value and a lower pKa value, as for diamines, the higher pka value is taken to be the highest pKa value in accordance with the present disclosure.

TABLE 1

| pKa Values for Representative Monoamines | |
|---|---|
| Pyrrolidine | 11.27 |
| Dibutyl amine | 11.25 |
| Piperidine | 11.12 |
| Diethylamine | 10.98 |
| Butylamine | 10.77 |
| Triethylamine | 10.75 |
| Dimethylamine | 10.73 |
| 2-Heptylamine | 10.70 |
| Propylamine | 10.69 |
| tert-Butylamine | 10.68 |
| Ethylamine | 10.67 |
| Heptylamine | 10.67 |
| Cyclohexylamine | 10.66 |
| Octylamine | 10.65 |
| Nonylamine | 10.64 |
| Decylamine | 10.64 |
| Pentylamine | 10.63 |
| Undecylamine | 10.63 |
| Dodecylamine | 10.63 |
| (Tridecyl)amine | 10.63 |
| Hexadecylamine | 10.63 |
| Tetradecylamine | 10.62 |
| Butylamine | 10.61 |
| Pentadecylamine | 10.61 |
| Octadecylamine | 10.60 |
| 2-Propanamine | 10.60 |
| sec-Butylamine | 10.60 |
| Methylamine | 10.59 |
| Hexylamine | 10.56 |

TABLE 1-continued pKa Values for Representative Monoamines

| | |
|---|---|
| iso-Butylamine | 10.43 |
| Trimethylamine | 9.81 |
| Allylamine | 9.49 |
| 2,4,6-trimethylpyridine | 7.43 |
| 2-Methylpyridine | 6.20 |
| 4-Methylpyridine | 6.08 |
| 2-Ethylpyridine | 5.89 |
| Acridine | 5.58 |
| Benzo[c]quinoline | 5.58 |
| 3-Methylpyridine | 5.52 |
| Isoquinoline | 5.42 |
| Pyridine | 5.23 |
| 2-Benzylpyridine | 5.13 |
| p-Toluidine | 5.08 |
| Quinoline | 4.90 |
| m-Toluidine | 4.71 |
| Aniline | 4.61 |
| o-Toluidine | 4.45 |
| 4-Aminobiphenyl | 4.35 |
| n-Allylaniline | 4.17 |
| 2-Naphthylamine | 4.16 |

TABLE 2

Higher pKa and Lower pKa Values for Representative Diamines

| Diamine | Higher pKa | Lower pKa |
|---|---|---|
| 1,2-Propandiamine | 9.82 | 6.61 |
| 1,3-Propandiamine | 10.55 | 8.88 |
| 1,4-butanediamine | 11.2 | 9.7 |
| 1,5-pentanediamine (25° C.) | 10.93 | 10.05 |
| 1,6-hexanediamine (25° C.) | 11.02 | 10.24 |
| Cis-1,2,cyclohexanediamine | 9.93 | 6.13 |
| Trans-1,2,cyclohexanediamine | 9.94 | 6.47 |
| p-Benzidine | 3.57 | 1.66 |
| 1,2-diaminobenzene | 4.74 | 0.6 |
| 1,3-diaminobenzene | 5.0 | 2.3 |
| 1,4-diaminobenzene | 6.2 | 2.7 |

For these amines, at pH of 1.0 pH unit above the highest pKa value, approximately 90% of the amine is in the non-valent form while at 2.0 pH units above the highest pKa value, approximately 99% of the amine is in the non-valent form Where the non-valent amine species is mostly formed, the solubility of the amine decreases significantly. Without being bound by theory, in embodiments where the increase in pH is combined with an increase in density, the decrease in solubility in combination with the increase in density of the aqueous mixture promotes the separation of the amine from the aqueous mixture. Thus, in preferred embodiments, the pH of the system should be high enough above the highest pKa value to form mostly or almost exclusively the non-valent amine species.

The degree of separation of the at least one amine from an aqueous mixture into the amine-rich layer may vary widely depending on the particular amine(s) present in the aqueous mixture and the conditions employed. In some exemplary embodiments, at least 60 wt. %, e.g., at least 70 wt. %, at least 80 wt. %, at least 90 wt. % or at least 95 wt. %, of the at least one amine that does not comprise an acidic group is separated into the amine-rich layer, based on the total amount of amine(s) present in the aqueous phase that do not contain acidic groups.

If present, as indicated above, any acidic amines contained in the aqueous mixture may or may not preferentially separate into the amine-rich layer. In some embodiments, for example, at least 50 wt. %, e.g., at least 60 wt. %, at least 70 wt. %, at least 80 wt. %, at least 90 wt. % or at least 95 wt. %, of the acidic amine may be separated into the amine-rich layer, based on the total amount of amine(s) present in the aqueous phase that contain acidic groups.

Addition of Salt

In some aspects, to improve the phase separation, the density of the aqueous mixture may also be increased by addition of salts. This can result in a clean secondary layer of concentrated amine (amine-rich layer) which can be physically separated from the aqueous layer containing water soluble impurities (for example, salts or acids). The steps of increasing the pH and the density may occur simultaneously or consecutively (in either order). By ensuring that the pH of the system is high enough above the highest pKa value to form mostly or almost exclusively the non-valent amine species (see, e.g., FIG. 10A (HMD speciation curves)), a wide range of salts could be added to the aqueous layer to increase its density in order to achieve the phase separation desired. In preferred embodiments, a salt is added to the aqueous mixture (or directly to the aqueous layer) in order to create a density difference between the amine-rich layer and the aqueous layer of at least 0.1 g/L.

For example, in one such aspect, the diamine HMD is concentrated from a dilute aqueous mixture by adjusting the pH to above 13.5 by the addition of a strong base such as sodium or potassium hydroxide. The density of the aqueous mixture is also increased such that the density difference between the aqueous layer and the amine-rich layer is at least 0.1 g/L through addition of additional strong base or other inorganic salts. This can result in a clean concentrated amine-rich layer comprising more than 20% wt. %, or higher than 30 wt. % HMD. This concentrated amine-rich layer can then be physically separated from the aqueous layer via phase separation.

In another related aspect, after the pH of the aqueous mixture has been adjusted to above 13.5, the HMD can be separated from the aqueous mixture by extraction with an organic solvent such as isopropanol, n-butanol, toluene or methylene chloride, for example.

Figure 7A:
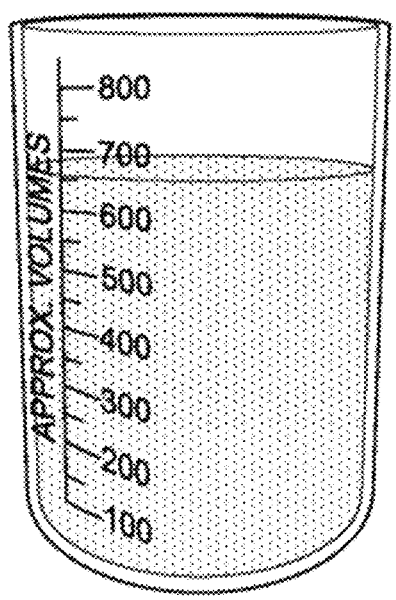
FIG. 7(a) shows an aqueous mixture containing amine which has been adjusted by adding 120 grams/liter NaOH in accordance with embodiments of the present disclosure.

FIG. 7 demonstrates the addition of a salt to improve phase separation. FIG. 7(a) shows a dilute amine-containing aqueous mixture where the pH has been adjusted by adding NaOH. As shown in the FIG. 7(a), when a lower NaOH concentration (120 g/L) was added to the dilute aqueous mixture containing 15.6 g of the diamine HMD, the resultant dilute aqueous HMD showed cloudiness, but not phase separation. Without being bound by theory, it is postulated that the insoluble non-valent HMD is immiscible but does not separate.

Figure 7B:
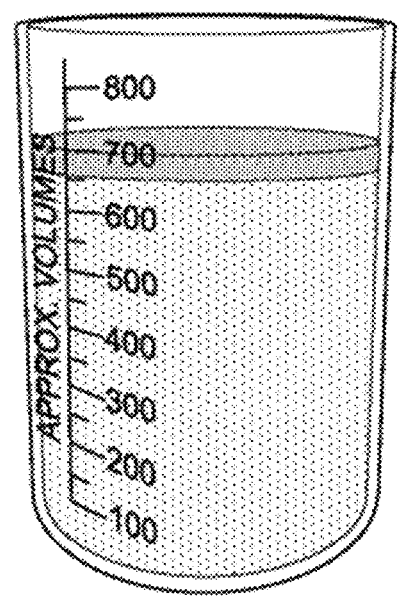
FIG. 7(b) shows a biphasic aqueous mixture containing amine which has been adjusted by adding 120 grams/liter NaOH and 154 grams of $Na_2SO_4$ to the solution in FIG. 1(a) in accordance with embodiments of the present disclosure.

By increasing the density of the aqueous layer by adding 154 g of sodium sulfate, the lower density concentrated HMD (approximately 40 wt. % HMD) forms a clean two-phase system, as shown in FIG. 7(b), with an HMD-rich top layer that can be physically separated from the bulk of the remaining aqueous layer and the salts contained in the aqueous layer. At 120 g/L NaOH and ~230 g/L $Na_2SO_4$, the difference between the density of the aqueous layer and the density of the concentrated HMD upper layer is expected to be greater than 0.2 g/L (see FIG. 9). Overall, this method from FIG. 7(b) gave a 16.6 times increase in HMD concentration (24 g/l to 408 g/L) and reduced the overall liquid volume by 22 times (650 mL to 30 mL). Even without accounting for the lower solubility of the sodium salts in the HMD-rich layer, a reduction in water soluble species (e.g., sodium salts) at the ratio of liquid reduction (22 times) or more is expected.

Any inorganic salt solution may be used to increase the density of the aqueous mixture and resulting aqueous layer.

Figure 9:
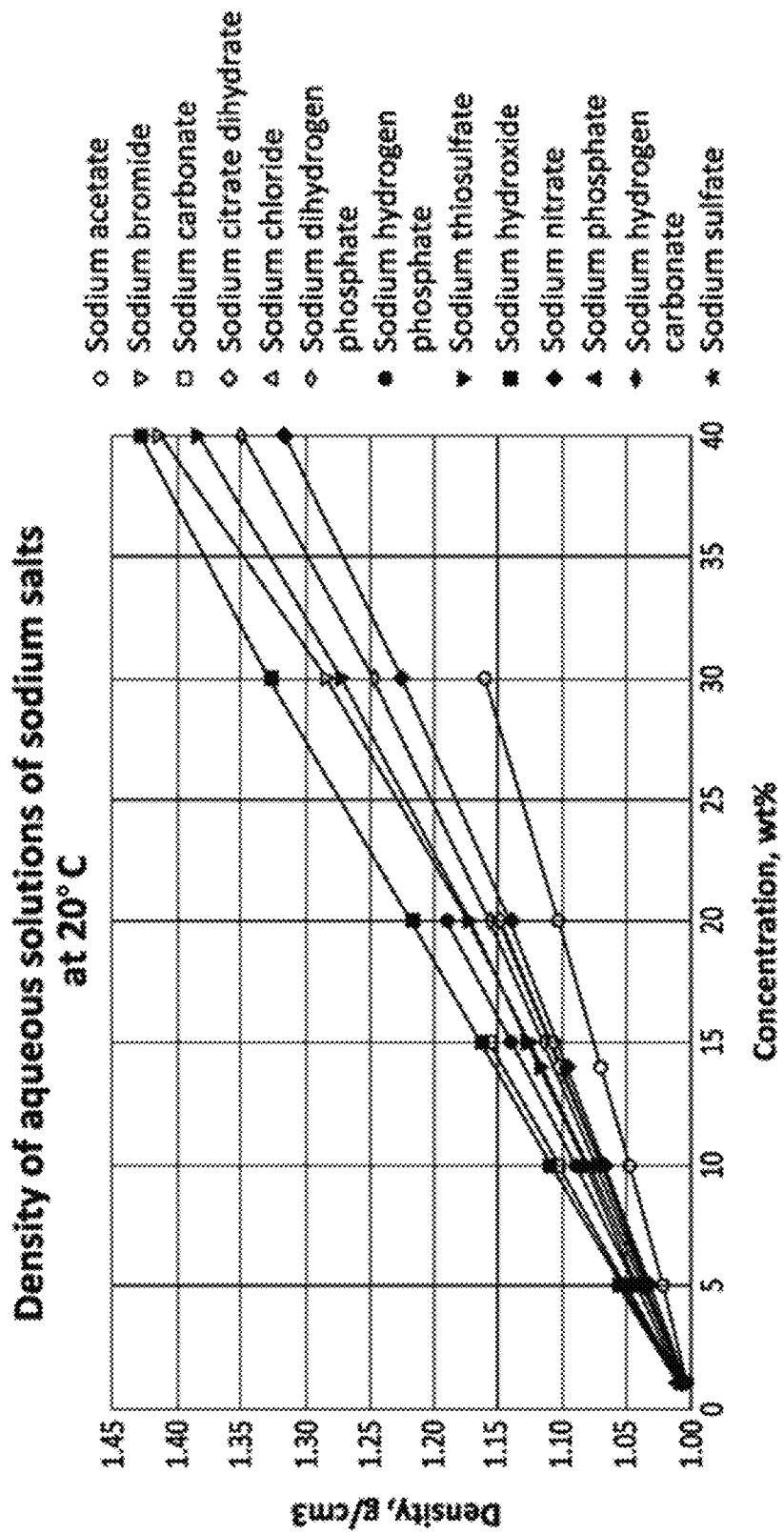
FIG. 9 shows the density of an aqueous mixture at different concentrations of various sodium salts to help illustrate embodiments of the present disclosure.

As an example, a range of aqueous solutions of sodium salts which could be used to increase the density of the aqueous mixture is shown in FIG. 9. Sodium salts may include, for example, sodium acetate, sodium bromide, sodium carbonate, sodium citrate dihydrate, sodium chloride, sodium dihydrogen phosphate, sodium hydrogen phosphate, sodium thiosulfate, sodium hydroxide, sodium nitrate, sodium phosphate, sodium hydrogen carbonate and sodium sulfate. FIG. 9 also shows how the density of an aqueous solution of the salts increases with increasing concentration. As shown in FIG. 9 for the sodium salts indicated, density increases nearly linearly with concentration over the conditions described.

Different salts affect the density of the aqueous solution differently. Salts that give a greater density lead to faster separation of the amine and are thus preferred. Inexpensive salts like sodium and potassium salts are also preferred because of their low cost. Salts that do not cause corrosive issues with the aqueous layer are also preferred in aspects where a salt is used.

The steps of increasing the pH and the density may occur simultaneously or consecutively. For example, as discussed above (including with reference to FIG. 7(b)), the steps of increasing the pH and the density may occur consecutively. However, when a very concentrated sodium hydroxide solution is used for elution, the very concentrated sodium hydroxide solution would by itself have a density of greater than about 1.2 g/L. In this latter situation, the steps of increasing the pH and density can occur simultaneously through the addition of the very concentrated sodium hydroxide.

Figure 8:
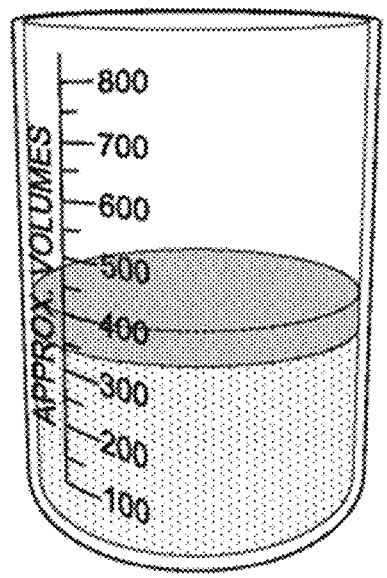
FIG. 8 shows an aqueous mixture containing amine which has been adjusted by adding 320 grams/liter NaOH in accordance with embodiments of the present disclosure.

FIG. 8 demonstrates an embodiment where an increase in pH and density can occur simultaneously. Layer separation without addition of sodium sulfate was observed when a more concentrated (320 g/L) NaOH solution that was used in connection with FIG. 7 was added to the aqueous HMD-containing mixture. The lighter layer in FIG. 8 contained approximately 14 g of HMD with an approximate 90 wt. % yield based on the amount of HMD in the aqueous mixture prior to addition of NaOH. For reference, 30 wt. % NaOH would by itself create a density difference between the amine-rich layer and the aqueous layer of at least 0.2 g/L. Thus, with a sufficiently concentrated and dense base, the steps of increasing the pH and the density can occur simultaneously.

As demonstrated in FIG. 7(b) and FIG. 8, using the methods according to the present disclosure, in some aspects a physical separation of the concentrated amine-rich layer can be obtained from an aqueous layer. In the chemical industry, such layer separations may be handled in various kinds of unit operations that are properly designed and operated for best separation efficiency. Such separations may be accomplished in batch, semi-continuous or continuous separation devices. One or more such separators may be sequenced to achieve effective separations. An example may include a phase separation device equipped with a hold time (volume) followed by an upright weir that overflows the top layer away from the bottom layer. Instrumentation/controls may be designed to appropriately maintain the layer boundary at a suitable location inside the device. Another example may include a vessel having a wide top section with tapering bottom section where the top layer accumulates in the wider section while the bottom layer is pumped out to maintain the layer boundary. In some cases, cyclonic separations may also be useful.

Some embodiments may involve integration with an ion-exchange unit to further purify the amine. For example, the majority of the amine could be separated from a dilute effluent stream from an amine fermentation, chemical manufacturing, or polymerization process using the teachings of the present disclosure. Then, subsequently an expensive technique such as ion exchange chromatography could be used to separate the rest of the amine at less overall processing effort and cost.

Figure 12:
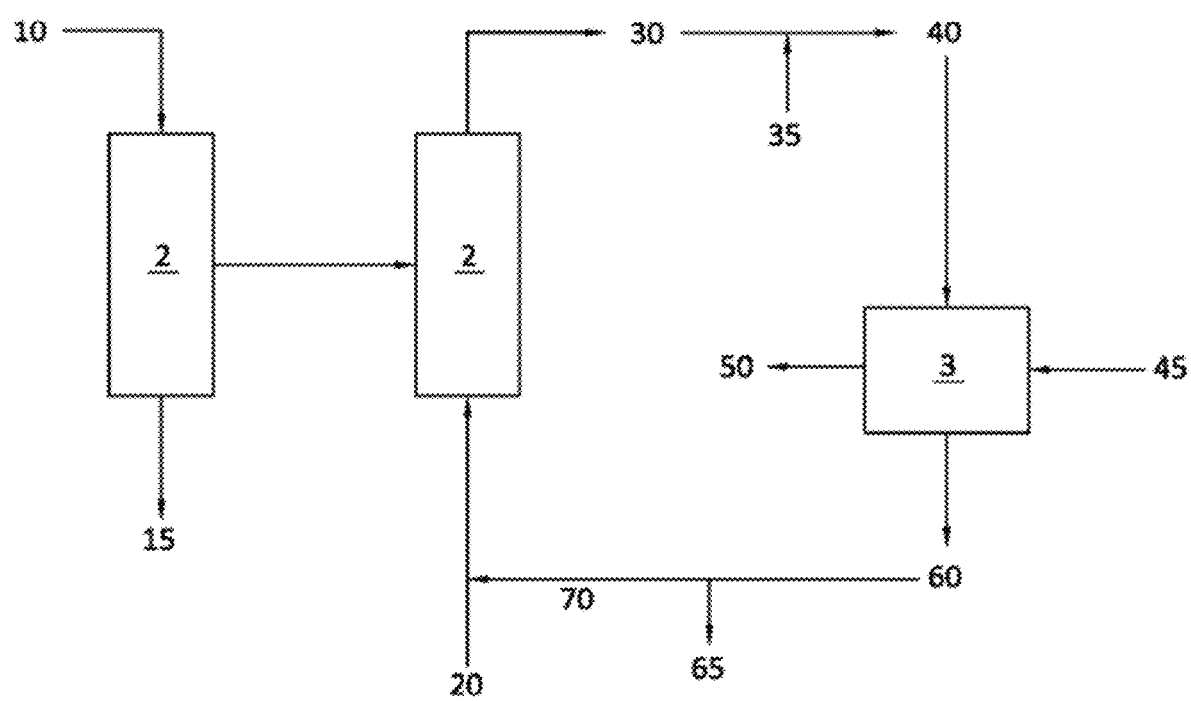
FIG. 12 shows an ion exchange integration with concentrated caustic eluent and recycle in accordance with embodiments of the present disclosure.

FIG. 12 demonstrates one embodiment involving an ion exchange resin column. In the embodiment shown in FIG. 12, an aqueous feed containing amine (10) is fed to a sulfonated ion exchange column containing resin (2). At least a portion of the amine is retained by the column (2) to produce an aqueous amine depleted stream (15). The column (2) loaded with amine is contacted with a strong base eluent (20) which removes at least a portion of the amine from the resin to produce an amine containing elution (30). As discussed, the pH of this elution is adjusted to at least 1.0 pH unit greater than the highest pKa value of the amine by the addition of a base (35) to produce a pH-adjusted amine containing elution (40). At least a portion of the non-valent species of the amine can then be extracted in an extractor (3) with organic solvent (45) (extractant) into an organic layer (50) (extract) and leaving a raffinate of an amine-depleted aqueous layer (60). In some aspects, this amine-depleted aqueous layer (60) can be recycled to be combined with the strong base eluent (20), which is fed to the sulfonated ion exchange column (2) after removing an aqueous purge stream (65).

Figure 13:
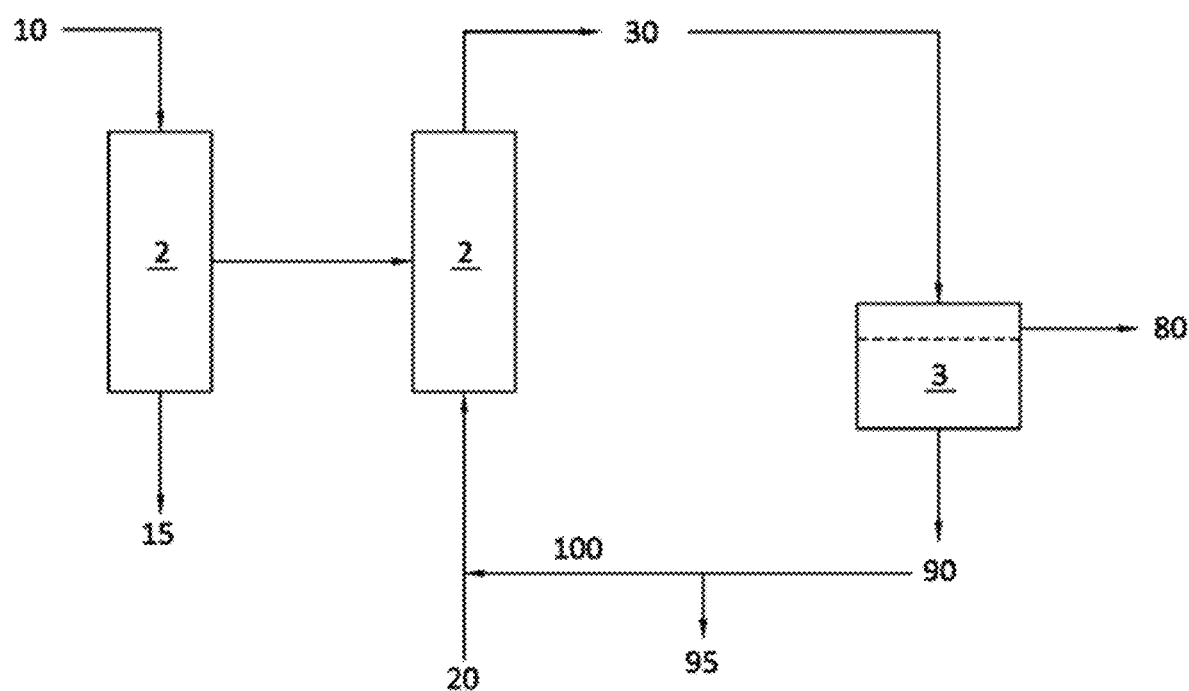

FIG. 13 shows another embodiment of the present disclosure. In the embodiment shown in FIG. 13, an aqueous feed containing amine (10) is fed to a sulfonated ion exchange column containing resin (2). At least a portion of the amine is retained by the column (2) to produce an aqueous amine depleted stream (15). The column (2) loaded with amine is contacted with a strong base eluent (20) which removes at least a portion of the amine from the resin to produce an amine containing elution (30). In the embodiment shown in FIG. 12, the pH of this elution after contact with the strong base eluent (20) is sufficient to form an amine-rich layer of at least a portion of the amine (in non-valent form) separate from the aqueous layer in a settler (3). After being fed to the settler (3), the amine-rich layer (80) containing at least a portion of the amine is separated from the amine depleted aqueous layer (90). In some aspects, this amine-depleted aqueous layer (90) can be recycled to be combined with the strong base eluent (20) fed to the sulfonated ion exchange column (2) after removing an aqueous purge stream (95).

Processes according to the present disclosure may also be integrated with several industrial chemical unit operations such as decanters, mixer-settlers, evaporators, distillative separations, extractive separations, crystallizers, filtration, cyclone separators, gas-liquid separators, chemical reactors, physi-sorption and/or chemi-sorption units, among others. A skilled person in the field of chemical processing will appreciate that the amines concentration increase operation according to the present disclosure can be integrated into a chemical flowsheet with material and energy balance closures.

EXAMPLES

The present disclosure will be better understood in view of the following non-limiting examples.

Example 1

An aqueous mixture comprising 5 wt. % hexamethylene diamine (HMD) at a pH of less than 10 was passed through a sodium exchanged sulfonated ion exchange resin and the HMD was adsorbed onto the resin to give a resin loading of 118 g HMD/L resin. The HMD was eluted off the ion exchange resin by passing 650 mL of 120 g/L sodium hydroxide eluting solution through the column to give 650 mL of solution containing 24 g/L HMD at pH of ~13 (total HMD=15.6 gr and 69 g/L of sodium ions (total sodium=45 gr) giving a sodium/HDM ratio of 2.88. This mixture is shown in FIG. 7(a). Then, 154 g of sodium sulfate was added to the stirred solution and the resultant mixture stirred until all of the added solids were dissolved. Stirring was stopped and the mixture was allowed to settle until a 35 mL top HMD-rich layer containing 400 g/L (total HMD recovered=14 g, 90% yield) formed. The HMD-rich layer contains less than 5.1 gr of sodium ions giving a sodium to sodium ratio of 0.37 which is a greater than 85% reduction in sodium to HMD ratio from the initial ratio in the eluent. This mixture with clear separation between the layers is shown in FIG. 7(b).

Example 2

An aqueous mixture comprising 5 wt. % hexamethylene diamine (HMD) at a pH of less than 10 was passed through a sodium exchanged sulfonated ion exchange resin and the HMD was adsorbed onto the resin to give a resin loading of 118 g HMD/L resin. The HMD was eluted off the ion exchange resin by passing 340 mL of a 320 g/L sodium hydroxide eluting solution (63 gr of sodium ions) through the column to give 400 mL of a mixture with a sodium to HMD ratio of 2.2. The mixture was allowed to settle until a 60 mL top HMD-rich layer containing 524 g/L (total HMD recovered=31.44 gr, 90% yield) formed. The resulting mixture with a clear separation between the layers is shown in FIG. 8. The HMD-rich layer contains 9.45 gr of sodium ion resulting in a sodium/HMD ratio 0.30 which is a greater than 85% reduction in sodium to HMD ratio.

Example 3

1 liter of fermentation broth containing 1 wt. % lysine and 4 wt. % pentamethylene diamine (PMD) at pH 6 was filtered to remove the biomass and other insoluble. The pH of the resulting solution was adjusted by addition of NaOH with stirring until a pH of greater than 13 was achieved. To the stirred solution, 200 g/L of sodium sulfate was added to bring the density of the aqueous layer to greater than 1.15 g/L. The resulting mixture was transferred to a separating funnel and two layers were allowed to separate. The lower salt-rich layer was drawn off to leave 100 mL of a PMD-rich layer containing 380 g/L of PMD (total PMD recovered 36 g; 90% yield).

Example 4

500 mL fermentation broth containing 1 wt. % lysine and 4 wt. % pentamethylene diamine (PMD) at pH 6 was filtered to remove the biomass and other insoluble. The pH of the resultant solution was adjusted by the addition of NaOH with stirring until a pH of greater than 13 was achieved. The resulting mixture was transferred to a separating funnel and extracted with 500 mL of n-butanol. The heavier aqueous was drawn off leaving a PMD-rich organic layer containing 3.5 wt. % PMD (17.5 g PMD recovered, 85% yield). The n-butanol was removed in a rotor evaporator leaving PMD with less than 2 wt. % lysine content.

Example 5

An aqueous mixture comprising 5 wt. % hexamethylene diamine (HMD) at a pH less than 10 was passed through a sodium exchanged sulfonated ion exchange resin and the HMD was adsorbed onto the resin to give a resin loading of 118 g HMD/L resin. The HMD was eluted off the ion exchange resin by passing 650 mL of 120 g/L sodium hydroxide eluting solution through the column to give 650 mL of solution containing 24 g/L HMD at pH of ~13 (total HMD=15.6 gr). The resultant mixture was transferred to a separating funnel and extracted with 500 mL of n-butanol. The heavier aqueous layer was drawn off to leave an HMD rich organic layer containing 4 wt. % PMD (12.5 g PMD recovered, 80% yield). The n-butanol was removed in a rotor evaporator leaving HMD with a low sodium concentration.

Figure 11:
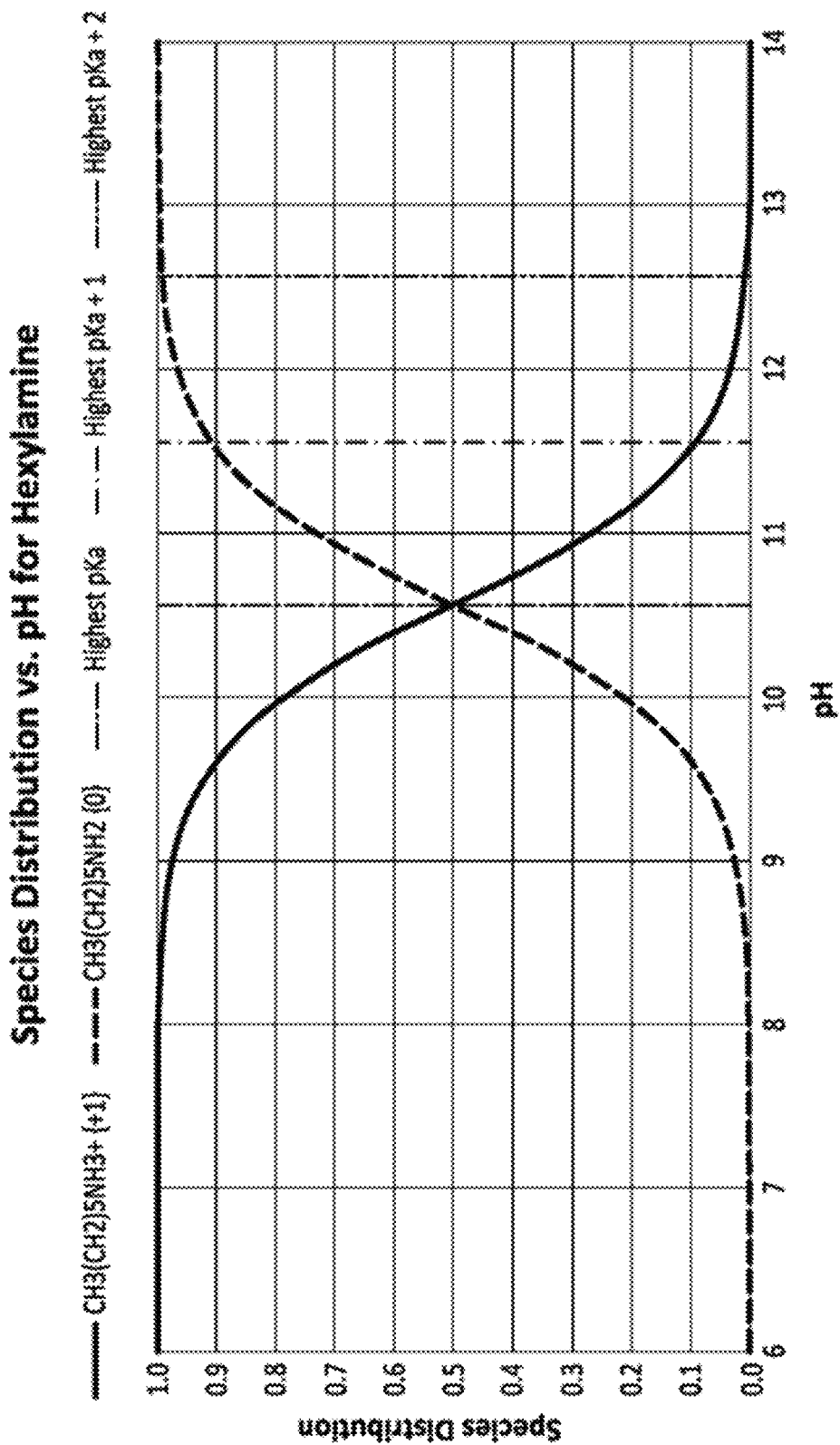
FIG. 11 shows an ion exchange integration with extraction and recycling of an aqueous layer in accordance with embodiments of the present disclosure.

A portion of the aqueous layer after the extraction was recycled and used for subsequent elutions from the ion exchange resin as shown in FIG. 11.

Example 6

An aqueous mixture comprising 5 wt. % hexamethylene diamine (HMD) at a pH less than 10 was passed through a sodium exchanged sulfonated ion exchange resin and the HMD was adsorbed onto the resin to give a resin loading of 118 g HMD/L resin. The HMD was eluted off the ion exchange resin by passing 340 mL of 320 g/L sodium hydroxide eluting solution through the column to give 400 mL of a mixture. The mixture was allowed to settle until a 60 mL top HMD-rich layer containing 524 g/L (total HMD recovered=31.44 g, 90% yield) formed.

A portion of the aqueous layer after the extraction was recycled and used for subsequent elutions from the ion exchange resin as shown in FIG. 12.

While the invention has been described in detail, modifications within the spirit and scope of the invention will be readily apparent to those of skill in the art. It should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by one of ordinary skill in the art. Furthermore, those of ordinary skill in the art will appreciate that the foregoing description is by way of example only and is not intended to limit the invention. All US patents and publications cited herein are incorporated by reference in their entirety.

Example 7

Several differing sodium salts were added to allow comparison of the effects of differing anions, specifically $Cl^-$, $SO_4^{2-}$, $CO_3^{2-}$, $NO_3^-$, $I^-$, and $PO_4^{3-}$, on the phase boundary. The various salts tested were added to solutions of 450 g/L HMD, 450 g/L NaOH, and water to achieve a concentration of 32.4 g/L of sodium, which is equivalent to 100 g/L of sodium sulphate. Samples of these salt solutions were then mixed together in varying ratios to provide final solutions with a range of HMD and NaOH concentrations, but all having the same salt concentration.

The salts were not completely soluble in the HMD and NaOH solutions at these concentrations, so some salt remained undissolved.

The phase boundary determined for each of the salts is shown in FIG. 1. The chloride and nitrate salts had very little effect from the established tie line model for phase boundary. Iodide salts increased the miscibility, thus making for worse phase separation. Carbonate and sulphate salts had decreased miscibility, improving separation. The phosphate salt formed a stable emulsion or gel even at very low concentrations and is not shown.

Figure 2:
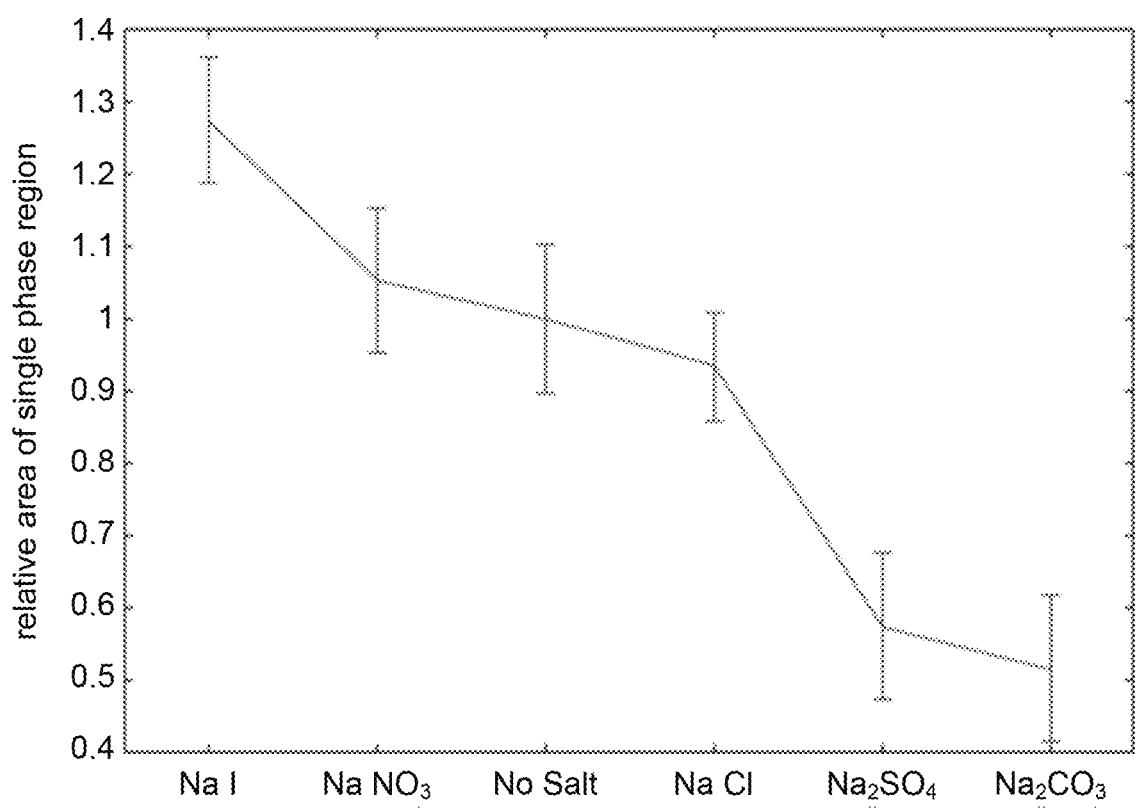
FIG. 2 shows the relative area of the single-phase region of an HMD and NaOH solution to which various sodium salts have been added. A higher relative area reflects a diminished two-phase region while a lower relative area reflects an expanded two-phase region.

The salts can be quantitatively compared by examining the area of the single phase region determined for each salt as shown in the graph of FIG. 2. A solution with a smaller single phase region area allows for phase separation more easily than a solution with a larger area. The results from a solution with no salt are included in FIG. 2 for comparison.

Example 8

Several different sulphate salts were added to investigate how the choice of cation affects the phase boundary. The cations tested were $K^+$, $Na^+$, $Ca^{2+}$, $Mg^{2+}$, $Zn^{2+}$, and $NH_4^+$. The salts were all present at 67.6 g/L of sulphate, which is equivalent to 100 g/L of sodium sulphate.

Solutions of 450 g/L HMD, 450 g/L NaOH, and water were made with these salt concentrations, and mixed together to create different HMD and NaOH concentrations, each solution having the same salt concentration. However, the salts were not completely soluble in the HMD and NaOH solutions at these concentrations, so there was some salt remaining undissolved.

Calcium and magnesium were unable to dissolve in sufficient quantities to be tested, and so were discounted.

Figure 3:
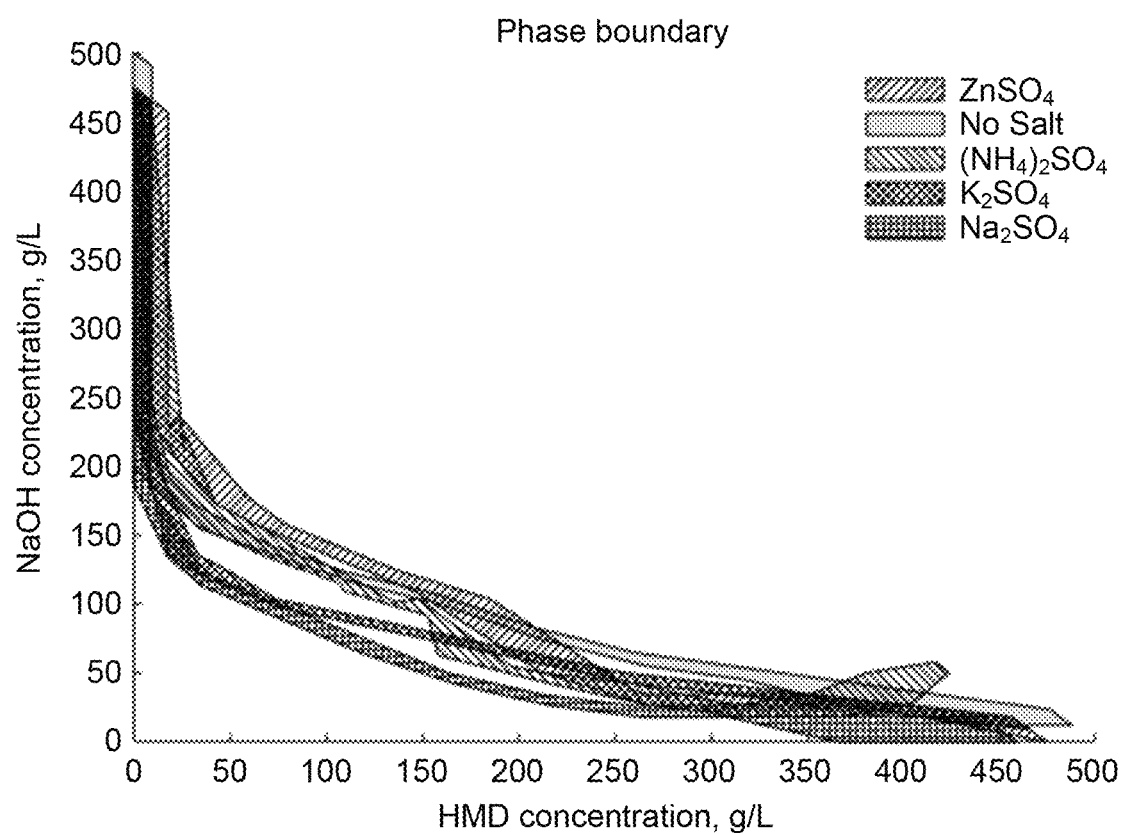
FIG. 3 shows a phase boundary diagram for an HMD and NaOH solution to which various sulphate salts have been added. The patterned areas represent the phase boundary lines between the single-phase region (below the line) and the two-phase (biphasic) region (above the line). The effect on the phase boundary obtained by the addition of various sulphate salts is demonstrated by comparison to the phase boundary of the solution with no additional salt.

In FIG. 3, the location of the phase boundary for each of these salts is represented as an uncertainty region defined between samples which were definitely single phase and those which were definitely two phase. Potassium and sodium salts reduced the area of the single phase region. This results in decreased miscibility between HMD and NaOH. The zinc and ammonium salts exhibited a peculiar behaviour in which the miscibility was increased at low HMD concentrations but reduced at high HMD concentrations. Ammonium, in particular, caused a lot of salt to precipitate out at very high HMD concentrations.

Figure 4:
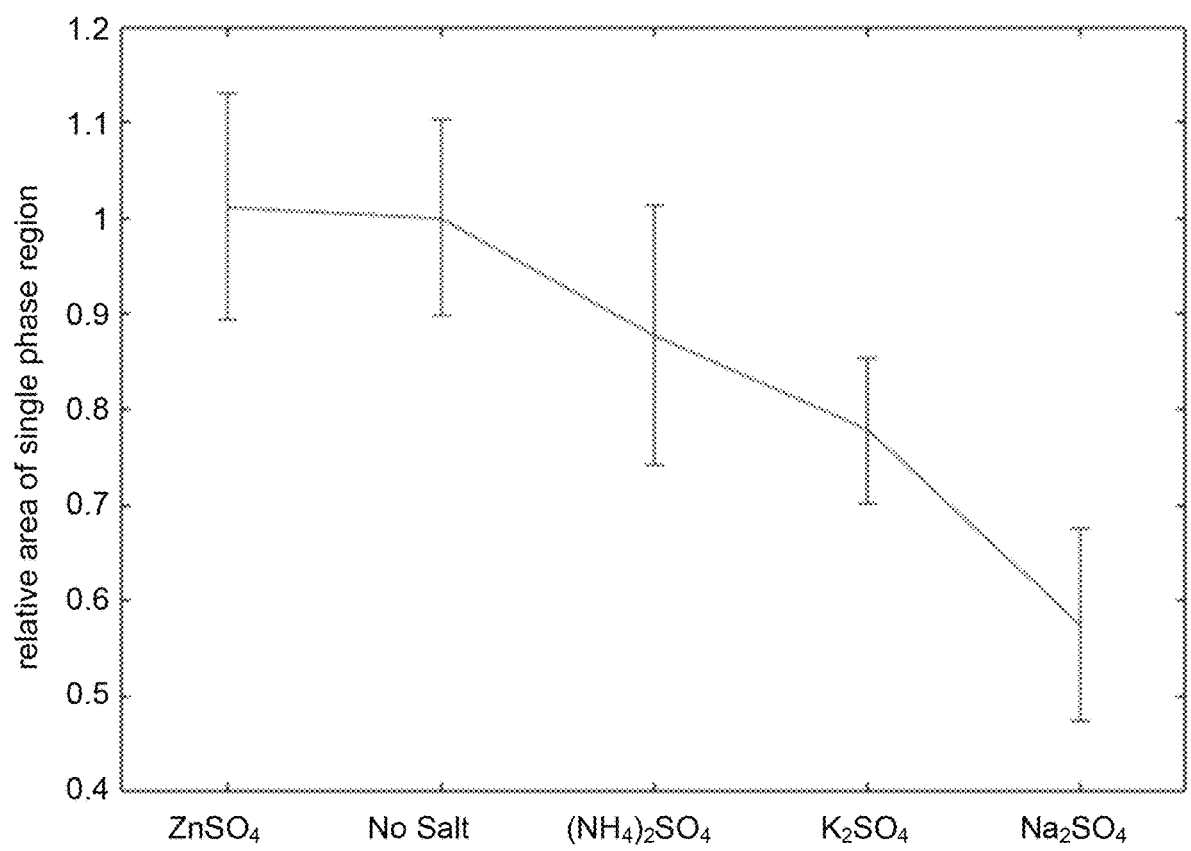
FIG. 4 shows the relative area of the single-phase region of an HMD and NaOH solution to which various sulphate salts have been added. A higher relative area reflects a diminished two-phase region while a lower relative area reflects an expanded two-phase region.

In FIG. 4, the salts are quantitatively compared by looking at the area of the single phase region on the graph. A solution with a smaller single phase region area allows for phase separation more easily than a solution with a larger area. Both FIG. 3 and FIG. 4 include a solution with no salt for comparison.

Example 9

A series of experiments were performed to demonstrate the effects of sodium sulphate, sodium carbonate, and additional sodium hydroxide on HMD recovery. The test solutions were compared to two base case solutions. The base case solution was prepared using 50 g/L and 100 g/L, respectively, HMD to which 1.5 charge equivalents of NaOH was added to push the HMD into its non-valent state. Butanol was used as the organic solvent in a volume ratio of 1:1. The test solutions were prepared in the same way but with the addition of 0.5 charge equivalents of either sulphate, carbonate, or additional sodium hydroxide.

It was observed that the fraction of the total volume given to the organic phase has a large influence on recovery. This can reliably be calculated from a mass balance of the butanol in the system, which is known to greater accuracy than the HMD. All samples showed a larger volume of organic phase than aqueous phase as a result of the higher solubility of water in butanol than vice versa. This data shows the same trends as in Examples 7 and 8, in terms of which salts increase or decrease the organic volume fraction.

Figure 5:
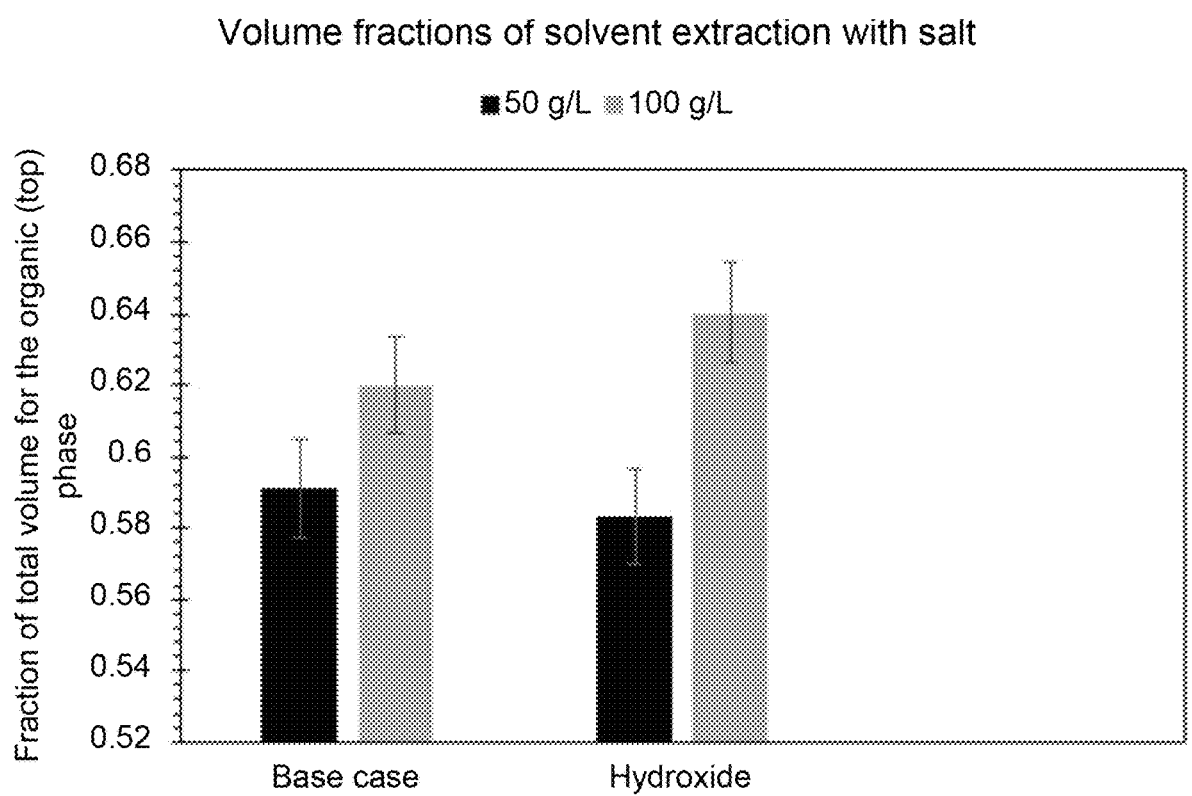
FIG. 5 shows a volume fraction diagram. The fraction of total volume of an aqueous-organic two-phase mixture that is contained in the organic phase is shown for an HMD solution at two different concentrations. In one case, no salt was added to the HMD solutions and in a second case additional sodium hydroxide was added.

The effectiveness of these salts on promoting solvent extraction depends on the concentration of HMD present in the system. Additional sodium hydroxide is beneficial to solvent extraction at high HMD concentrations, as shown in FIG. 5.

Exemplary Embodiment Set 1

1. A method of separating at least one amine, from an aqueous mixture, wherein said at least one amine does not comprise an acidic group, comprising:
   providing an aqueous mixture comprising water and the at least one amine having a highest pKa value;
   increasing the pH of the aqueous mixture to at least 1.0 pH unit above the highest pKa value;
   forming an aqueous layer and an amine-rich layer, wherein the amine-rich layer comprises the at least one amine; and
   separating the amine-rich layer from the aqueous layer.

2. The method according to embodiment 1, wherein the aqueous mixture comprises the amine in a concentration less than 20 wt. %.

3. The method according to any of embodiments 1 or 2, wherein the aqueous mixture comprises the amine in a concentration less than 15 wt. %.

4. The method according to any of embodiments 1-3, wherein the aqueous mixture comprises the amine in a concentration less than 10 wt. %.

5. The method according to any of embodiments 1-4, wherein the pH of the aqueous mixture is increased at least 2.0 pH units above the highest pKa value for the at least one amine.

6. The method according to any of embodiments 1-5, wherein said at least one amine is a monoamine, a diamine or a triamine.

7. The method according to any of embodiments 1-6, wherein said at least one amine comprises 1,4-diaminobutane, pentamethylenediamine, hexamethylenediamine, heptamethylenediamine, hexyl amine, nonyl amine, aminonitrile, diethylenetriamine, or combinations thereof.

8. The method according to any of embodiments 1-7, wherein the step of increasing the pH of the aqueous mixture to at least 1.0 pH unit above the highest pKa value for the at least one amine results in the formation of a non-valent species of the amine in a concentration of greater than 90 wt. %.

9. The method according to embodiment 5, wherein the step of increasing the pH of the aqueous mixture to at least 2.0 pH units above the highest pKa value for the at least one amine results in the formation of a non-valent species of the amine in a concentration of greater than 99 wt. %.

10. The method according to any of embodiments 1-9, comprising the step of changing the density difference between the amine-rich layer and the aqueous layer to at least 0.1 g/L.

11. The method according to embodiment 10, wherein the density difference between the amine-rich layer and the aqueous layer is at least 0.2 g/L.

12. The method according to any of embodiments 10 or 11, wherein the density difference between the amine-rich layer and the aqueous layer is at least 0.3 g/L.

13. The method according to any of embodiments 10-12, wherein said steps of increasing the pH of the aqueous mixture to above the highest pKa value for the at least one amine and changing the density difference between the amine-rich layer and the aqueous layer occur simultaneously.

14. The method according to embodiment 13, wherein said steps occur simultaneously by addition of a concentrated strong basic alkaline solution.

15. The method according to any of embodiments 10-12, wherein said steps of increasing the pH of the aqueous mixture to above the highest pKa value for the at least one amine and changing the density difference between the amine-rich layer and the aqueous layer occur consecutively.

16. The method according to embodiment 15, wherein said steps occur consecutively by further addition of one or more inorganic salts to the aqueous mixture or the aqueous layer.

17. The method according to embodiment 16, wherein said one or more inorganic salts comprises sodium salts, calcium, or potassium salts.

18. The method according to any of embodiments 1-17, wherein said step of separating said amine-rich layer from the aqueous layer comprises the process of physical separation or the process of extraction.

19. The method according to embodiment 18, wherein said process of extraction comprises contacting said aqueous layer with an organic solvent which is at least partially immiscible with water.

20. The method according to any of embodiments 18 or 19, wherein said extraction is a continuous process.

21. The method according to any of embodiments 18-20, wherein said extraction is via one or more mixer settler systems.

22. The method according to embodiment 19, wherein said organic solvent is capable of dissolving said at least one amine.

23. The method according to any of embodiments 19 or 22, wherein said organic solvent comprises isopropyl alcohol, n-butanol, toluene, cyclohexane, methylene chloride, or a combination thereof.

24. The method according to any of embodiments 1-23, wherein said aqueous mixture is derived from an ion exchange elution, hydrolyzed polyamide polymer, fermentation broth, dilute stream from an amine production process, or dilute aqueous effluent stream from polyamide polymerization.

25. The method according to embodiment 24, wherein said hydrolyzed polyamide polymer comprises nylon-6,6, nylon-4,6, nylon-4,10, nylon-5,6, nylon-6,10, or nylon-6,12.

26. The method according to any of embodiments 1-25, wherein said amine-rich layer has an amine concentration of more than 30 wt. %.

27. A method of reducing the salt to amine ratio in an aqueous mixture comprising at least one amine comprising the steps of:
increasing the pH of the aqueous mixture to a pH where a non-valent species of the least one amine is formed in an amount greater than 90 wt. % of the total amount of the at least one amine;
forming an amine-rich layer and an aqueous layer, wherein the amine-rich layer is immiscible in the aqueous layer; and
separating said amine-rich layer from the aqueous layer.

28. The method according to embodiment 27, wherein the salt to amine ratio is reduced by 85%.

29. The method according to embodiment 28, wherein the salt to amine ratio is reduced by 75%.

30. The method according to any of embodiments 27-29, wherein the non-valent species is formed in an amount greater than 98 wt. % of the total amount of the at least one amine.

31. The method according to any of embodiments 27-30, wherein the amine-rich layer is separated from the aqueous layer by the process of physical separation or by extraction.

32. The method according to embodiment 31, wherein in said physical separation or extraction, the difference between the densities of the amine-rich layer and the aqueous layer is at least 0.1 g/L.

33. The method according to embodiment 32, wherein the steps of adjusting the pH and changing the density difference between the amine-rich layer and the aqueous layer to at least 0.1 g/L occur simultaneously.

34. The method according to embodiment 33, wherein said steps occur simultaneously by addition of a concentrated strong basic alkaline solution.

35. The method according to embodiment 32, wherein the steps of adjusting the pH and changing the density difference between the amine-rich layer and the aqueous layer to at least 0.1 g/L occur consecutively.

36. The method according to embodiment 35, wherein said steps occur consecutively by addition of one or more inorganic salts to the aqueous mixture or the aqueous layer.

37. The method according to embodiment 36, wherein said one or more inorganic salts comprises sodium salts or potassium salts.

38. The method according to any of embodiments 31-37, wherein the process of extraction comprises contacting said aqueous mixture with an organic solvent which is at least partially immiscible with water.

39. The method according to embodiment 38, wherein said organic solvent is capable of dissolving said at least one amine.

40. The method according to any of embodiments 38 and 39, wherein said organic solvent comprises isopropyl alcohol, n-butanol, toluene, cyclohexane, methylene chloride, or a combination thereof.

41. The method according to any of embodiments 27-40, wherein said pH is increased to pH 12.5 or more.

42. The method according to embodiment 41, wherein said pH is increased to pH 12.5 or more by addition of an alkaline solution.

43. A method of separating amines from aqueous mixtures containing acidic species comprising the steps of:
increasing the pH of an aqueous mixture comprising acidic species and at least one amine to a pH where (1) a non-valent species of the least one amine is formed in an amount greater than 90 wt. % of the total amount of the at least one amine, and (2) at least a portion of the non-valent species of the at least one amine is not soluble in the aqueous mixture; and
separating said amine-rich portion from the mixture.

44. A method according to embodiment 43, wherein the acidic species comprises carboxylic acids or amines containing acidic moieties.

45. A method according to any of embodiments 43 or 44, wherein the acidic species comprises an amino-acid, α-amino acid or an Ω-amino acid.

46. A method according to any of embodiments 43-45, wherein the at least one amine comprises a diamine and the acidic species comprises an amino acid.

47. The method according to any of embodiments 43-46, wherein the aqueous mixture is derived from a chemical and/or fermentation process.

48. The method according to embodiment 47, wherein said process comprises decarboxylation of lysine.

49. The method according to embodiment 47, wherein said method comprises separating PMD from a process of decarboxylation of lysine.

50. The method according to embodiment 47, wherein said process comprises amination of adipic acid or 6-aminocaproic acid.

51. The method according to embodiment 47, wherein said method comprises separating HMD from a process of amination of adipic acid or 6-aminocaproic acid.

52. A method of recovering at least one amine from an aqueous mixture comprising:
contacting an ion exchange resin with the aqueous mixture comprising the at least one amine to produce a resin containing at least a portion of the at least one amine;
treating the resin containing the at least a portion of the at least one amine with a base eluent to produce an amine-containing elution;
adjusting the pH of the amine-containing elution to at least 1.0 pH unit above the highest pKa value for the at least one amine; and
recovering the at least one amine.

53. The method according to embodiment 52, wherein the recovery step comprises physically separating the amine containing elution after adjusting its pH into an amine-rich layer and an amine depleted aqueous layer, and removing the amine-rich layer.

54. The method according to embodiment 53, wherein the recovery step comprises addition of a salt to the eluent to improve the physical separation of the amine containing elution after adjusting its pH.

55. The method according to any one of embodiments 53 and 54, wherein the recovery step comprises extracting the amine containing elution after adjusting its pH with an organic solvent to produce an amine containing organic layer comprising at least a portion of the at least one amine and the amine depleted aqueous layer.

56. The method according to any one of embodiments 53-55, further comprising recycling at least a portion of the amine depleted aqueous layer to the base eluent and treating the resin containing at least a portion of the at least one amine with the combined base eluent and at least a portion of the amine depleted aqueous layer.

57. A system for performing the method of any one of embodiments 52-57, comprising an ion exchange resin for conducting the contacting step and a settler for conducting the recovery step.

58. A system for performing the method of any one of embodiments 52-57, comprising an ion exchange resin for conducting the contacting step and an extractor for conducting the recovery step.

Exemplary Embodiment Set 2

1. A method of separating at least one amine, from an aqueous mixture, wherein said at least one amine does not comprise an acidic group, comprising:
providing an aqueous mixture comprising water and the at least one amine having a highest pKa value;
increasing the pH of the aqueous mixture to at least 1.0 pH unit above the highest pKa value;
forming an aqueous layer and an amine-rich layer, wherein the amine-rich layer comprises the at least one amine; and
separating the amine-rich layer from the aqueous layer.

2. The method according to embodiment 1, wherein the aqueous mixture comprises the amine in a concentration less than 20 wt. %.

3. The method according to embodiment 2, wherein the aqueous mixture comprises the amine in a concentration less than 15 wt. %.

4. The method according to embodiment 3, wherein the aqueous mixture comprises the amine in a concentration less than 10 wt. %.

5. The method according to embodiment 1, wherein the pH of the aqueous mixture is increased at least 2.0 pH units above the highest pKa value for the at least one amine.

6. The method according to embodiment 1, wherein said at least one amine is a monoamine, a diamine or a triamine.

7. The method according to embodiment 6, wherein said at least one amine comprises 1,4-diaminobutane, pentamethylenediamine, hexamethylenediamine, heptamethylenediamine, hexyl amine, nonyl amine, aminonitrile, diethylenetriamine, or combinations thereof.

8. The method according to embodiment 1, wherein the step of increasing the pH of the aqueous mixture to at least 1.0 pH unit above the highest pKa value for the at least one amine results in the formation of a non-valent species of the amine in a concentration of greater than 90 wt. %.

9. The method according to embodiment 5, wherein the step of increasing the pH of the aqueous mixture to 2.0 pH units above the highest pKa value for the at least one amine results in the formation of a non-valent species of the amine in a concentration of greater than 99 wt. %.

10. The method according to embodiment 1, comprising the step of changing the density difference between the amine-rich layer and the aqueous layer to at least 0.1 g/L.

11. The method according to embodiment 10, wherein the density difference between the amine-rich layer and the aqueous layer is at least 0.2 g/L.

12. The method according to embodiment 11, wherein the density difference between the amine-rich layer and the aqueous layer is at least 0.3 g/L.

13. The method according to embodiment 10, wherein said steps of increasing the pH of the aqueous mixture to above the highest pKa value for the at least one amine and changing the density difference between the amine-rich layer and the aqueous layer to at least 0.1 g/L occur simultaneously.

14. The method according to embodiment 13, wherein said steps occur simultaneously by addition of a concentrated strong basic alkaline solution.

15. The method according to embodiment 10, wherein said steps of increasing the pH of the aqueous mixture to above the highest pKa value for the at least one amine and changing the density difference between the amine-rich layer and the aqueous layer to at least 0.1 g/L occur consecutively.

16. The method according to embodiment 15, wherein said steps occur consecutively by further addition of one or more inorganic salts to the aqueous mixture or the aqueous layer.

17. The method according to embodiment 16, wherein said one or more inorganic salts comprises sodium salts, calcium, or potassium salts.

18. The method according to embodiment 1, wherein said step of separating said amine-rich layer from the aqueous layer comprises the process of physical separation or the process of extraction.

19. The method according to embodiment 18, wherein said process of extraction comprises contacting said aqueous layer with an organic solvent which is at least partially immiscible with water.

20. The method according to embodiment 19, wherein said extraction is a continuous process.

21. The method according to embodiment 19, wherein said extraction is via one or more mixer settler systems.

22. The method according to embodiment 19, wherein said organic solvent is capable of dissolving said at least one amine.

23. The method according to embodiment 22, wherein said organic solvent comprises isopropyl alcohol, n-butanol, toluene, cyclohexane, methylene chloride, or a combination thereof.

24. The method according to embodiment 1, wherein said aqueous mixture is derived from an ion exchange elution, hydrolyzed polyamide polymer, fermentation broth, dilute stream from an amine production process, or dilute aqueous effluent stream from polyamide polymerization.

25. The method according to embodiment 24, wherein said hydrolyzed polyamide polymer comprises nylon-6,6, nylon-4,6, nylon-4,10, nylon-5,6, nylon-6,10, or nylon-6,12.

26. The method according to embodiment 1, wherein said amine-rich layer has an amine concentration of more than 30 wt. %.

27. A method of reducing the salt to amine ratio in an aqueous mixture comprising at least one amine comprising the steps of:
increasing the pH of the aqueous mixture to a pH where a non-valent species of the least one amine is formed in an amount greater than 90 wt. % of the total amount of the at least one amine;
forming an amine-rich layer and an aqueous layer, wherein the amine-rich layer is immiscible in the aqueous layer; and
separating said amine-rich layer from the aqueous layer.

28. The method according to embodiment 27, wherein the salt to amine ratio is reduced by 85%.

29. The method according to embodiment 28, wherein the salt to amine ratio is reduced by 75%.

30. The method according to embodiment 27, wherein the non-valent species is formed in an amount greater than 98 wt. % of the total amount of the at least one amine.

31. The method according to embodiment 27, wherein the amine-rich layer is separated from the aqueous layer by the process of physical separation or by extraction.

32. The method according to embodiment 31, wherein in said physical separation or extraction, the difference between the densities of the amine-rich layer and the aqueous layer is at least 0.1 g/L.

33. The method according to embodiment 32, wherein the steps of adjusting the pH and changing the density difference between the amine-rich layer and the aqueous layer to at least 0.1 g/L occur simultaneously.

34. The method according to embodiment 33, wherein said steps occur simultaneously by addition of a concentrated strong basic alkaline solution.

35. The method according to embodiment 32, wherein the steps of adjusting the pH and changing the density difference between the amine-rich layer and the aqueous layer to at least 0.1 g/L occur consecutively.

36. The method according to embodiment 35, wherein said steps occur consecutively by addition of one or more inorganic salts to the aqueous mixture or the aqueous layer.

37. The method according to embodiment 36, wherein said one or more inorganic salts comprises sodium salts or potassium salts.

38. The method according to embodiment 27, wherein the process of extraction comprises contacting said aqueous mixture with an organic solvent which is at least partially immiscible with water.

39. The method according to embodiment 38, wherein said organic solvent is capable of dissolving said at least one amine.

40. The method according to embodiment 39, wherein said organic solvent comprises isopropyl alcohol, n-butanol, toluene, cyclohexane, methylene chloride, or a combination thereof.

41. The method according to embodiment 27, wherein said pH is increased to pH 12.5 or more.

42. The method according to embodiment 41, wherein said pH is increased to pH 12.5 or more by addition of an alkaline solution.

43. A method of separating amines from aqueous mixtures containing acidic species comprising the steps of:
increasing the pH of an aqueous mixture comprising acidic species and at least one amine to a pH where (1) a non-valent species of the least one amine is formed in an amount greater than 90 wt. % of the total amount of the at least one amine, and (2) at least a portion of the non-valent species of the at least one amine is not soluble in the aqueous mixture; and
separating said amine-rich portion from the mixture.

44. The method according to embodiment 43, wherein the acidic species comprises carboxylic acids or amines containing acidic moieties.

45. The method according to embodiment 44, wherein the acidic species comprises an amino-acid, $\alpha$-amino acid or an $\Omega$-amino acid.

46. The method according to embodiment 43, wherein the at least one amine comprises a diamine and the acidic species comprises an amino acid.

47. The method according to embodiment 43, wherein the aqueous mixture is derived from a chemical and/or fermentation process.

48. The method according to embodiment 47, wherein said process comprises decarboxylation of lysine.

49. The method according to embodiment 47, wherein said method comprises separating PMD from a process of decarboxylation of lysine.

50. The method according to embodiment 47, wherein said process comprises amination of adipic acid or 6-aminocaproic acid.

51. The method according to embodiment 47, wherein said method comprises separating HMD from a process of amination of adipic acid or 6-aminocaproic acid.

52. A method of recovering at least one amine from an aqueous mixture comprising:
contacting an ion exchange resin with the aqueous mixture comprising the at least one amine to produce a resin containing at least a portion of the at least one amine;
treating the resin containing the at least a portion of the at least one amine with a base eluent to produce an amine-containing elution;
adjusting the pH of the amine-containing elution to at least 1.0 pH unit above the highest pKa value for the at least one amine; and
recovering the at least one amine.

53. The method according to embodiment 52, wherein the recovery step comprises physically separating the amine containing elution after adjusting its pH into an amine-rich layer and an amine depleted aqueous layer, and removing the amine-rich layer.

54. The method according to embodiment 53, wherein the recovery step comprises addition of a salt to the base eluent to improve the physical separation of the amine containing elution after adjusting its pH.

55. The method according to embodiment 53, wherein the recovery step comprises extracting the amine containing elution after adjusting its pH with an organic solvent to produce an amine containing organic layer comprising at least a portion of the at least one amine and the amine depleted aqueous layer.

56. The method according to embodiment 53, further comprising recycling at least a portion of the amine depleted aqueous layer to the base eluent and treating the resin containing at least a portion of the at least one amine with the combined base eluent and at least a portion of the amine depleted aqueous layer.

57. A system for performing the method of embodiment 52, comprising an ion exchange resin for conducting the contacting step and a settler for conducting the recovery step.

58. A system for performing the method of embodiment 52, comprising an ion exchange resin for conducting the contacting step and an extractor for conducting the recovery step.

Exemplary Embodiment Set 3

1. A method of separating diamines from aqueous fermentation broth containing acidic species comprising the steps of:
   increasing the pH of an aqueous fermentation broth comprising acidic species and at least one diamine to a pH where (1) a non-valent species of the least one diamine is formed in an amount greater than 90 wt. % of the total amount of the at least one diamine, and (2) at least a portion of the non-valent species of the at least one diamine is not soluble in the aqueous fermentation broth; and
   separating the diamine-rich portion from the fermentation broth.
2. A method according to embodiment 1, wherein the acidic species comprises carboxylic acids or amines containing acidic moieties.
3. A method according to any of embodiments 1 or 2, wherein the acidic species comprises an amino-acid, α-amino acid or an Ω-amino acid.
4. A method according to any of embodiments 1-3, wherein the at least one amine comprises a diamine and the acidic species comprises an amino acid.
5. The method according to any of embodiments 1-4, wherein the aqueous fermentation broth is derived from a chemical and/or fermentation process.
6. The method according to embodiment 5, wherein the process comprises decarboxylation of lysine.
7. The method according to embodiment 5, wherein the method comprises separating PMD from a process of decarboxylation of lysine.
8. The method according to embodiment 5, wherein the process comprises amination of adipic acid or 6-aminocaproic acid.
9. The method according to embodiment 5, wherein the method comprises separating HMD from a process of amination of adipic acid or 6-aminocaproic acid.

What is claimed is:
1. A method comprising:
   providing a single-phase aqueous fermentation broth comprising water and a diamine that does not comprise an acidic group;
   increasing the pH of the aqueous fermentation broth by addition of a quantity of a strong basic alkaline solution to at least 1.0 pH unit above the highest pKa value of the diamine, wherein adding the strong basic alkaline solution causes the aqueous fermentation broth to form a biphasic solution comprising an aqueous layer and a diamine-rich layer wherein the diamine-rich layer comprises the diamine; and
   separating the diamine-rich layer from the aqueous layer.
2. The method of claim 1, wherein the quantity of the strong basic alkaline solution added is greater than a minimum amount required to form the biphasic solution.
3. The method according to claim 1, wherein the aqueous fermentation broth is filtered.
4. The method according to claim 1, wherein the aqueous fermentation broth comprises a total amount of diamine in a concentration less than 20 wt. %.
5. The method according to claim 1, wherein the pH of the aqueous fermentation broth is increased at least 2.0 pH units above the highest pKa value of the diamine.
6. The method according to claim 1, wherein the diamine comprises a carbon chain length of C4, C5, C6, C7, C8, C9, C10, C11, or C12.
7. The method according to claim 1, wherein increasing the pH of the aqueous fermentation broth results in formation of a non-valent species of the diamine in a concentration of greater than 90 wt. % of the total amount of diamine.
8. The method according to claim 1, further comprising changing the density of either the aqueous fermentation broth or the aqueous layer in order to achieve a density difference between the diamine-rich layer and the aqueous layer of at least 0.1 g/L by addition of the strong basic alkaline solution.
9. The method according to claim 8, wherein increasing the pH of the aqueous fermentation broth and changing the density of the aqueous fermentation broth occur simultaneously.
10. The method according to claim 9, wherein increasing the pH of the aqueous fermentation broth and changing the density of the aqueous fermentation broth occur simultaneously by addition of the strong basic alkaline solution.
11. The method according to claim 8, wherein increasing the pH of the aqueous fermentation broth and changing the density of the aqueous fermentation broth or the aqueous layer occur consecutively.
12. The method according to claim 11, wherein changing the density of the aqueous fermentation broth or the aqueous layer occurs by addition of one or more inorganic salts to the aqueous fermentation broth or the aqueous layer.
13. The method according to claim 12, wherein the one or more inorganic salts comprise sodium salts and/or potassium salts.
14. The method according to claim 13, wherein the one or more inorganic salts are chosen from sodium sulphate, sodium carbonate, potassium sulphate, and potassium carbonate.
15. The method according to claim 1, wherein the method is performed at a temperature less than 42° C.
16. The method according to claim 1, wherein separating the diamine-rich layer from the aqueous layer comprises a physical separation process or an extraction process.
17. The method according to claim 16, further comprising adding sodium hydroxide to the aqueous fermentation broth or the aqueous layer.

18. The method according to claim 16, wherein the extraction process comprises contacting the aqueous layer with an organic solvent that is at least partially immiscible with water, wherein the organic solvent comprises isopropyl alcohol, n-butanol, toluene, cyclohexane, methylene chloride, or combinations thereof.

19. The method according to claim 1, wherein the diamine-rich layer has a diamine concentration of more than 30 wt. %.

20. A method of reducing a salt to diamine ratio, comprising:
providing an aqueous fermentation broth comprising salt and a diamine;
increasing the pH of the aqueous fermentation broth to a pH level at which a non-valent species of the diamine is formed in an amount greater than 90 wt. % of the total amount of the diamine;
forming a diamine-rich layer and an aqueous layer by addition of a concentrated strong basic alkaline solution or at least one inorganic salt to the aqueous fermentation broth, wherein adding the strong basic alkaline solution causes the aqueous fermentation broth to form a biphasic solution, and wherein the diamine-rich layer is immiscible in the aqueous layer and comprises a reduced salt to diamine ratio relative to the aqueous fermentation broth; and
separating the diamine-rich layer from the aqueous layer.

21. The method according to claim 20, wherein the salt to diamine ratio is reduced by at least 85% or at least 75%.

22. The method according to claim 20, wherein the amount of the non-valent species formed is greater than 98 wt. % of the total amount of the diamine.

23. The method according to claim 20, wherein the diamine-rich layer is separated from the aqueous layer by a physical separation or by an extraction.

24. The method according to claim 23, wherein the physical separation or extraction comprises changing a density difference between the diamine-rich layer and the aqueous layer to at least 0.1 g/L.

25. The method according to claim 24, wherein increasing the pH of the aqueous fermentation broth and changing the density difference between the diamine-rich layer and the aqueous layer occur simultaneously.

26. The method according to claim 25, wherein increasing the pH of the aqueous fermentation broth and changing the density difference between the diamine-rich layer and the aqueous layer occur simultaneously by addition of a concentrated strong basic alkaline solution.

27. The method according to claim 24, wherein increasing the pH of the aqueous fermentation broth and changing the density difference between the diamine-rich layer and the aqueous layer occur consecutively.

28. The method according to claim 27, wherein increasing the pH of the aqueous fermentation broth and changing the density difference between the diamine-rich layer and the aqueous layer occur consecutively by addition of at least one inorganic salt to the aqueous fermentation broth or the aqueous layer.

29. The method according to claim 28, wherein the inorganic salt comprises a salt chosen from sodium salts and potassium salts.

30. The method according to claim 28, wherein the at least one inorganic salt is chosen from sodium sulphate, sodium carbonate, potassium sulphate, and potassium carbonate.

31. The method according to claim 20, wherein the method is performed at a temperature below 42° C.

32. The method according to claim 23, wherein the extraction process comprises contacting the aqueous fermentation broth with an organic solvent that is at least partially immiscible with water, wherein the organic solvent comprises isopropyl alcohol, n-butanol, toluene, cyclohexane, methylene chloride, or combinations thereof.

33. The method according to claim 23, further comprising adding sodium hydroxide to the aqueous fermentation broth or the aqueous layer.

34. The method according to claim 20, wherein the pH of the aqueous fermentation broth is increased to a pH level of 12.5 or higher.

35. The method according to claim 34, wherein the pH of the aqueous fermentation broth is increased to a pH level of 12.5 or higher by addition of an alkaline solution.

36. A method of recovering a diamine from an aqueous fermentation broth, comprising:
providing an aqueous fermentation broth comprising a diamine;
contacting an ion exchange resin with the aqueous fermentation broth to produce a resin containing at least a portion of the diamine;
treating the resin with a base eluent to produce a diamine-containing elution;
adjusting the pH of the diamine-containing elution to at least 1.0 pH unit above the highest pKa value of the diamine; and
recovering the diamine.

37. The method according to claim 36, wherein recovering the diamine comprises adjusting the pH of the diamine-containing elution, physically separating the diamine-containing elution after adjusting its pH into a diamine-rich layer and a diamine-depleted aqueous layer, and removing the diamine-rich layer.

38. The method according to claim 36, wherein recovering the diamine further comprises adding a salt to the diamine-containing elution.

39. The method according to claim 37, wherein physically separating the diamine-containing elution comprises extracting the diamine-containing elution with an organic solvent to produce the diamine-rich layer comprising at least a portion of the diamine and the organic solvent, and the diamine-depleted aqueous layer.

40. The method according to claim 36, further comprising recycling at least a portion of the diamine-depleted aqueous layer to the base eluent and treating the resin containing at least a portion of the diamine with the combined base eluent and at least a portion of the diamine-depleted aqueous layer.

41. The method according to claim 36, wherein contacting the ion exchange resin with the aqueous fermentation broth is repeated after recovering the diamine.

* * * * *